(12) United States Patent
Dutta et al.

(10) Patent No.: US 11,213,616 B2
(45) Date of Patent: Jan. 4, 2022

(54) RECHARGE SOLUTION FOR ZIRCONIUM PHOSPHATE

(71) Applicant: Medtronic, Inc., Minneapolis, MN (US)

(72) Inventors: Sukalyan Dutta, Bangalore (IN); Bryant J. Pudil, Plymouth, MN (US); Krishnaraja Nellikunje, Bangalore (IN); Christopher M. Hobot, Rogers, MN (US); Kanjimpuredathil Muralikrishna Menon, Bangalore (IN)

(73) Assignee: Medtronic, Inc., Minneapolis, MN (US)

( * ) Notice: Subject to any disclaimer, the term of this patent is extended or adjusted under 35 U.S.C. 154(b) by 113 days.

(21) Appl. No.: 16/458,336

(22) Filed: Jul. 1, 2019

(65) Prior Publication Data

US 2020/0061269 A1 Feb. 27, 2020

(30) Foreign Application Priority Data

Aug. 24, 2018 (IN) .............................. 201841031852

(51) Int. Cl.
*A61M 1/16* (2006.01)
*B01J 20/02* (2006.01)

(52) U.S. Cl.
CPC ........ *A61M 1/1696* (2013.01); *A61M 1/1601* (2014.02); *B01J 20/0211* (2013.01)

(58) Field of Classification Search
CPC .... A61M 1/16; A61M 1/1696; A61M 1/1601; B01J 20/02; B01J 20/0211
USPC ...................................................... 502/27
See application file for complete search history.

(56) References Cited

U.S. PATENT DOCUMENTS

| | | |
|---|---|---|
| 1,617,288 A | 2/1927 | Kenney |
| 2,703,313 A | 1/1950 | Gill |
| 3,608,729 A | 9/1971 | Haselden |
| 3,617,545 A | 11/1971 | Dubois |
| 3,617,558 A | 11/1971 | Jones |
| 3,669,878 A | 6/1972 | Marantz |
| 3,669,880 A | 6/1972 | Marantz |
| 3,776,819 A | 12/1973 | Williams |
| 3,840,835 A | 10/1974 | Kussy |
| 3,850,835 A | 11/1974 | Marantz |
| 3,884,808 A | 5/1975 | Scott |
| 3,902,490 A | 9/1975 | Jacobsen |
| 3,989,622 A | 11/1976 | Marantz |
| 4,060,485 A | 11/1977 | Eaton |
| 4,073,725 A | 2/1978 | Takeuchi |
| 4,094,775 A | 6/1978 | Mueller |
| 4,142,845 A | 3/1979 | Lepp |
| 4,192,748 A | 3/1980 | Hyden |
| 4,206,054 A | 6/1980 | Moore |
| 4,209,392 A | 6/1980 | Wallace |
| 4,269,708 A | 5/1981 | Bonomini |
| 4,371,385 A | 2/1983 | Johnson |
| 4,374,382 A | 2/1983 | Markowitz |
| 4,376,707 A | 3/1983 | Lehmann |
| 4,381,999 A | 5/1983 | Boucher |
| 4,460,555 A | 7/1984 | Thompson |
| 4,556,063 A | 12/1985 | Thompson |
| 4,562,751 A | 1/1986 | Nason |
| 4,581,141 A | 4/1986 | Ash |
| 4,612,122 A | 9/1986 | Ambrus |
| 4,650,587 A | 3/1987 | Polak |
| 4,661,246 A | 4/1987 | Ash |
| 4,678,408 A | 7/1987 | Mason |
| 4,684,460 A | 8/1987 | Issautier |
| 4,685,903 A | 8/1987 | Cable |
| 4,687,582 A | 8/1987 | Dixon |
| 4,750,494 A | 6/1988 | King |
| 4,765,907 A | 8/1988 | Scott |
| 4,826,663 A | 5/1989 | Alberti |
| 4,828,693 A | 5/1989 | Lindsay |
| 5,032,615 A | 7/1991 | Ward et al. |
| 5,047,014 A | 9/1991 | Mosebach et al. |
| 5,080,653 A | 1/1992 | Voss |
| 5,092,886 A | 3/1992 | Dobos-Hardy |
| 5,097,122 A | 3/1992 | Coiman |
| 5,127,404 A | 7/1992 | Wyborny |
| 5,192,132 A | 3/1993 | Pelensky |
| 5,230,702 A | 7/1993 | Lindsay |
| 5,284,470 A | 2/1994 | Beltz |
| 5,302,288 A | 4/1994 | Meidl |
| 5,305,745 A | 4/1994 | Zacouto |
| 5,308,315 A | 5/1994 | Khuri |

(Continued)

FOREIGN PATENT DOCUMENTS

| | | |
|---|---|---|
| CN | 1487853 A | 4/2004 |
| CN | 102573618 | 7/2012 |

(Continued)

OTHER PUBLICATIONS

Chinese Office Action for App. No. 201711179528.X, dated Jul. 27, 2020.
U.S. Appl. No. 13/100,847, filed Nov. 10, 2011, C-Tech BioMedical Inc.
U.S. Appl. No. 13/565,733, filed Aug. 2, 2012, Medtronic.
U.S. Appl. No. 13/757,693, filed Feb. 1, 2013, Medtronic.
U.S. Appl. No. 13/757,709, filed Feb. 1, 2013, Medtronic.
U.S. Appl. No. 13/757,728, filed Feb. 1, 2013, Medtronic.
U.S. Appl. No. 13/836,538, filed Mar. 15, 2013, Medtronic.
U.S. Appl. No. 61/760,033, filed Feb. 1, 2013, Medtronic.
U.S. Appl. No. 14/637,606_OA.
U.S. Appl. No. 14/645,394_OA.

(Continued)

*Primary Examiner* — Edward M Johnson

(57) ABSTRACT

The invention relates to devices, systems, and methods for mixing one or more solutions to generate a recharge solution having specified concentrations of a sodium salt and acid for recharging and disinfecting zirconium phosphate in reusable sorbent modules. The devices, systems, and methods can generate a recharge solution by a sorbent recharger that is introduced through the sorbent module to recharge and to disinfect the zirconium phosphate.

17 Claims, 4 Drawing Sheets

(56) References Cited

U.S. PATENT DOCUMENTS

| | | |
|---|---|---|
| 5,318,750 A | 6/1994 | Laspombes |
| 5,399,157 A | 3/1995 | Goux |
| 5,441,049 A | 8/1995 | Masano |
| 5,442,969 A | 8/1995 | Troutner |
| 5,445,610 A | 8/1995 | Evert |
| 5,468,388 A | 11/1995 | Goddard |
| 5,507,723 A | 4/1996 | Keshaviah |
| 5,662,806 A | 9/1997 | Keshaviah et al. |
| 5,683,432 A | 11/1997 | Goedeke |
| 5,685,988 A | 11/1997 | Malchesky |
| 5,716,400 A | 2/1998 | Davidson |
| 5,744,031 A | 4/1998 | Bene |
| 5,762,782 A | 6/1998 | Kenley |
| 5,770,086 A | 6/1998 | Indriksons |
| 5,849,179 A | 12/1998 | Emerson |
| 5,858,186 A | 1/1999 | Glass |
| 5,938,634 A | 8/1999 | Packard |
| 5,938,938 A | 8/1999 | Bosetto |
| 5,944,684 A | 8/1999 | Roberts |
| 6,036,858 A | 3/2000 | Carlsson |
| 6,048,732 A | 4/2000 | Anslyn |
| 6,052,622 A | 4/2000 | Holmstrom |
| 6,058,331 A | 5/2000 | King |
| 6,114,176 A | 9/2000 | Edgson et al. |
| 6,126,831 A | 10/2000 | Goldau |
| 6,171,480 B1 | 1/2001 | Lee |
| 6,230,059 B1 | 5/2001 | Duffin |
| 6,248,093 B1 | 6/2001 | Moberg |
| 6,254,567 B1 | 7/2001 | Treu |
| 6,321,101 B1 | 11/2001 | Holmstrom |
| 6,362,591 B1 | 3/2002 | Moberg |
| 6,363,279 B1 | 3/2002 | Ben-Haim |
| 6,390,969 B1 | 5/2002 | Bolling et al. |
| 6,491,993 B1 | 12/2002 | Forbes |
| 6,521,184 B1 | 2/2003 | Edgson et al. |
| 6,554,798 B1 | 4/2003 | Mann |
| 6,555,986 B2 | 4/2003 | Moberg |
| 6,565,525 B1 | 5/2003 | Burbank et al. |
| 6,572,769 B2 | 6/2003 | Rajan |
| 6,579,460 B1 | 6/2003 | Willis |
| 6,585,675 B1 | 7/2003 | O'Mahony et al. |
| 6,589,229 B1 | 7/2003 | Connelly |
| 6,593,747 B2 | 7/2003 | Puskas |
| 6,596,234 B1 | 7/2003 | Schnell et al. |
| 6,602,399 B1 | 8/2003 | Fromherz |
| 6,627,164 B1 | 9/2003 | Wong |
| 6,666,840 B1 | 12/2003 | Falkvall et al. |
| 6,676,608 B1 | 1/2004 | Keren |
| 6,695,807 B2 | 2/2004 | Bell et al. |
| 6,711,439 B1 | 3/2004 | Bradley |
| 6,719,745 B1 | 4/2004 | Taylor |
| 6,773,412 B2 | 8/2004 | O'Mahony et al. |
| 6,814,724 B2 | 11/2004 | Taylor |
| 6,818,196 B2 | 11/2004 | Wong |
| 6,861,266 B1 | 3/2005 | Sternby |
| 6,878,258 B2 | 4/2005 | Hughes |
| 6,878,283 B2 | 4/2005 | Thompson |
| 6,878,285 B2 | 4/2005 | Hughes |
| 6,890,315 B1 | 5/2005 | Levin |
| 6,923,782 B2 | 8/2005 | O'Mahony et al. |
| 6,960,179 B2 | 11/2005 | Gura |
| 7,029,456 B2 | 4/2006 | Ware et al. |
| 7,033,498 B2 | 4/2006 | Wong |
| 7,077,819 B1 | 7/2006 | Goldau |
| 7,097,630 B2 | 8/2006 | Gotch |
| 7,101,519 B2 | 9/2006 | Wong |
| 7,128,750 B1 | 10/2006 | Stergiopulos |
| 7,153,693 B2 | 12/2006 | Tajiri |
| 7,208,092 B2 | 4/2007 | Micheli |
| 7,241,272 B2 | 7/2007 | Karoor |
| 7,276,042 B2 | 10/2007 | Polaschegg |
| 7,309,323 B2 | 12/2007 | Gura |
| 7,318,892 B2 | 1/2008 | Connell |
| 7,326,576 B2 | 2/2008 | Womble et al. |
| 7,384,543 B2 | 6/2008 | Jonsson et al. |
| 7,435,342 B2 | 10/2008 | Tsukamoto |
| 7,462,161 B2 | 12/2008 | O'Mahony et al. |
| 7,488,447 B2 | 2/2009 | Sternby |
| 7,537,688 B2 | 5/2009 | Tarumi |
| 7,544,300 B2 | 6/2009 | Brugger |
| 7,544,737 B2 | 6/2009 | Poss |
| 7,563,240 B2 | 7/2009 | Gross |
| 7,566,432 B2 | 7/2009 | Wong |
| 7,575,564 B2 | 8/2009 | Childers |
| 7,597,806 B2 | 10/2009 | Uchi |
| 7,674,231 B2 | 3/2010 | McCombie |
| 7,674,237 B2 | 3/2010 | O'Mahony et al. |
| 7,686,778 B2 | 3/2010 | Burbank et al. |
| 7,704,361 B2 | 4/2010 | Garde |
| 7,736,507 B2 | 6/2010 | Wong |
| 7,754,852 B2 | 7/2010 | Burnett |
| 7,756,572 B1 | 7/2010 | Fard |
| 7,776,001 B2 | 8/2010 | Brugger et al. |
| 7,776,006 B2 | 8/2010 | Childers |
| 7,776,210 B2 | 8/2010 | Rosenbaum |
| 7,794,141 B2 | 9/2010 | Perry |
| 7,794,419 B2 | 9/2010 | Paolini |
| 7,850,635 B2 | 12/2010 | Polaschegg |
| 7,867,214 B2 | 1/2011 | Childers |
| 7,901,376 B2 | 3/2011 | Steck et al. |
| 7,905,853 B2 | 3/2011 | Chapman et al. |
| 7,922,686 B2 | 4/2011 | Childers |
| 7,922,911 B2 | 4/2011 | Micheli |
| 7,947,179 B2 | 5/2011 | Rosenbaum |
| 7,955,289 B2 | 6/2011 | O'Mahony et al. |
| 7,955,290 B2 | 6/2011 | Karoor |
| 7,967,022 B2 | 6/2011 | Grant |
| 7,981,082 B2 | 7/2011 | Wang |
| 7,988,854 B2 | 8/2011 | Tsukamoto |
| 8,002,726 B2 | 8/2011 | Karoor |
| 8,012,118 B2 | 9/2011 | Curtin |
| 8,029,454 B2 | 10/2011 | Kelly |
| 8,034,161 B2 | 10/2011 | Gura |
| 8,066,658 B2 | 11/2011 | Karoor |
| 8,070,709 B2 | 12/2011 | Childers |
| 8,080,161 B2 | 12/2011 | Ding et al. |
| 8,087,303 B2 | 1/2012 | Beavis |
| 8,096,969 B2 | 1/2012 | Roberts |
| 8,180,574 B2 | 5/2012 | Lo |
| 8,182,673 B2 | 5/2012 | Childers et al. |
| 8,183,046 B2 | 5/2012 | Lu |
| 8,187,250 B2 | 5/2012 | Roberts |
| 8,197,439 B2 | 6/2012 | Wang |
| 8,206,591 B2 | 6/2012 | Kotanko et al. |
| 8,211,048 B2 | 7/2012 | Szamosfalvi et al. |
| 8,221,529 B2 | 7/2012 | Childers et al. |
| 8,226,595 B2 | 7/2012 | Childers et al. |
| 8,246,826 B2 | 8/2012 | Wilt |
| 8,267,881 B2 | 9/2012 | O'Mahony et al. |
| 8,273,049 B2 | 9/2012 | Demers |
| 8,292,594 B2 | 10/2012 | Tracey |
| 8,303,532 B2 | 11/2012 | Hamada |
| 8,313,642 B2 | 11/2012 | Yu |
| 8,317,492 B2 | 11/2012 | Demers |
| 8,357,113 B2 | 1/2013 | Childers |
| 8,357,298 B2 | 1/2013 | Demers et al. |
| 8,366,316 B2 | 2/2013 | Kamen |
| 8,366,655 B2 | 2/2013 | Kamen |
| 8,376,999 B2 | 2/2013 | Busby et al. |
| 8,377,012 B2 | 2/2013 | Chapman et al. |
| 8,377,308 B2 | 2/2013 | Kreymann et al. |
| 8,388,567 B2 | 3/2013 | Rovatti |
| 8,404,491 B2 | 3/2013 | Li |
| 8,409,441 B2 | 4/2013 | Wilt |
| 8,409,444 B2 | 4/2013 | Wong |
| 8,449,487 B2 | 5/2013 | Hovland et al. |
| 8,480,607 B2 | 7/2013 | Davies |
| 8,499,780 B2 | 8/2013 | Wilt |
| 8,518,260 B2 | 8/2013 | Raimann |
| 8,535,525 B2 | 9/2013 | Heyes |
| 8,580,112 B2 | 11/2013 | Updyke |
| 8,597,227 B2 | 12/2013 | Childers |
| 8,647,506 B2 | 2/2014 | Wong |
| 8,696,626 B2 | 4/2014 | Kirsch |

(56) References Cited

U.S. PATENT DOCUMENTS

| | | |
|---|---|---|
| 8,733,559 B2 | 5/2014 | Wong |
| 8,764,981 B2 | 7/2014 | Ding |
| 8,777,892 B2 | 7/2014 | Sandford |
| 8,903,492 B2 | 12/2014 | Soykan |
| 9,144,640 B2 | 9/2015 | Pudil |
| 9,254,355 B2 | 2/2016 | Sandford |
| 9,527,015 B2 | 12/2016 | Chau |
| 2001/0007931 A1 | 7/2001 | Blatter |
| 2001/0009756 A1 | 7/2001 | Hei et al. |
| 2002/0016550 A1 | 2/2002 | Sweeney |
| 2002/0027106 A1 | 3/2002 | Smith |
| 2002/0042561 A1 | 4/2002 | Schulman |
| 2002/0062098 A1 | 5/2002 | Cavicchioli et al. |
| 2002/0112609 A1 | 8/2002 | Wong |
| 2002/0117436 A1 | 8/2002 | Rajan |
| 2003/0080059 A1 | 5/2003 | Peterson |
| 2003/0097086 A1 | 5/2003 | Gura |
| 2003/0105435 A1 | 6/2003 | Taylor |
| 2003/0113931 A1 | 6/2003 | Pan |
| 2003/0114787 A1 | 6/2003 | Gura |
| 2003/0138348 A1 | 7/2003 | Bell et al. |
| 2003/0187479 A1 | 10/2003 | Thong |
| 2004/0019312 A1 | 1/2004 | Childers |
| 2004/0019320 A1 | 1/2004 | Childers |
| 2004/0030277 A1 | 2/2004 | O'Mahony et al. |
| 2004/0037986 A1 | 2/2004 | Houston et al. |
| 2004/0054315 A1 | 3/2004 | Levin et al. |
| 2004/0082903 A1 | 4/2004 | Micheli |
| 2004/0084358 A1 | 5/2004 | O'Mahony et al. |
| 2004/0099593 A1 | 5/2004 | DePaolis |
| 2004/0147900 A1 | 7/2004 | Polaschegg |
| 2004/0168963 A1 | 9/2004 | King |
| 2004/0215090 A1 | 10/2004 | Erkkila |
| 2004/0257409 A1 | 12/2004 | Cheok |
| 2005/0006296 A1 | 1/2005 | Sullivan |
| 2005/0056592 A1 | 3/2005 | Braunger |
| 2005/0065760 A1 | 3/2005 | Murtfeldt |
| 2005/0101901 A1 | 5/2005 | Gura |
| 2005/0113796 A1 | 5/2005 | Taylor |
| 2005/0126961 A1 | 6/2005 | Bissler |
| 2005/0131332 A1 | 6/2005 | Kelly |
| 2005/0126998 A1 | 7/2005 | Childers |
| 2005/0148923 A1 | 7/2005 | Sternby |
| 2005/0150832 A1 | 7/2005 | Tsukamoto |
| 2005/0230313 A1 | 10/2005 | O'Mahony et al. |
| 2005/0234354 A1 | 10/2005 | Rowlandson |
| 2005/0234381 A1 | 10/2005 | Niemetz |
| 2005/0274658 A1 | 12/2005 | Rosenbaum |
| 2006/0025661 A1 | 2/2006 | Sweeney |
| 2006/0037483 A1 | 2/2006 | Kief |
| 2006/0217771 A1 | 2/2006 | Soykan |
| 2006/0157413 A1 | 7/2006 | Bene |
| 2006/0189926 A1 | 8/2006 | Hall et al. |
| 2006/0195064 A1 | 8/2006 | Plahey |
| 2006/0226079 A1 | 10/2006 | Mori |
| 2006/0241543 A1 | 10/2006 | Gura |
| 2006/0241709 A1 | 10/2006 | Soykan |
| 2006/0264894 A1 | 11/2006 | Moberg |
| 2007/0007208 A1 | 1/2007 | Brugger |
| 2007/0055296 A1 | 3/2007 | Stergiopulos |
| 2007/0066928 A1 | 3/2007 | Lannoy |
| 2007/0138011 A1 | 6/2007 | Hofmann |
| 2007/0175827 A1 | 8/2007 | Wariar |
| 2007/0179431 A1 | 8/2007 | Roberts |
| 2007/0213665 A1 | 9/2007 | Curtin |
| 2007/0215545 A1 | 9/2007 | Bissler |
| 2007/0243113 A1 | 10/2007 | DiLeo |
| 2007/0255250 A1 | 11/2007 | Moberg |
| 2008/0006570 A1 | 1/2008 | Gura |
| 2008/0011664 A1 | 1/2008 | Karoor |
| 2008/0015493 A1 | 1/2008 | Childers et al. |
| 2008/0021337 A1 | 1/2008 | Li |
| 2008/0051696 A1 | 2/2008 | Curtin |
| 2008/0053905 A9 | 3/2008 | Brugger |
| 2008/0067132 A1 | 3/2008 | Ross |
| 2008/0215247 A1 | 9/2008 | Tonelli |
| 2008/0217245 A1 | 9/2008 | Rambod |
| 2008/0241031 A1 | 10/2008 | Li |
| 2008/0292935 A1 | 11/2008 | Roelofs |
| 2009/0020471 A1 | 1/2009 | Tsukamoto |
| 2009/0078636 A1 | 3/2009 | Uchi |
| 2009/0084199 A1 | 4/2009 | Wright |
| 2009/0101552 A1 | 4/2009 | Fulkerson |
| 2009/0101577 A1 | 4/2009 | Fulkerson |
| 2009/0120864 A1 | 5/2009 | Fulkerson |
| 2009/0127193 A1 | 5/2009 | Updyke |
| 2009/0216045 A1 | 8/2009 | Singh |
| 2009/0266358 A1 | 10/2009 | Rock |
| 2009/0275849 A1 | 11/2009 | Stewart |
| 2009/0275883 A1 | 11/2009 | Chapman |
| 2009/0281484 A1 | 11/2009 | Childers |
| 2009/0282980 A1 | 11/2009 | Gura |
| 2010/0004588 A1 | 1/2010 | Yeh |
| 2010/0007838 A1 | 1/2010 | Fujimoto |
| 2010/0010429 A1 | 1/2010 | Childers |
| 2010/0030151 A1 | 2/2010 | Kirsch |
| 2010/0051552 A1 | 3/2010 | Rohde |
| 2010/0078381 A1 | 4/2010 | Merchant |
| 2010/0078387 A1 | 4/2010 | Wong |
| 2010/0084330 A1 | 4/2010 | Wong |
| 2010/0094158 A1 | 4/2010 | Solem |
| 2010/0100027 A1 | 4/2010 | Schilthuizen |
| 2010/0101195 A1 | 4/2010 | Clements |
| 2010/0102190 A1 | 4/2010 | Zhu et al. |
| 2010/0114012 A1 | 5/2010 | Sandford |
| 2010/0137693 A1 | 6/2010 | Porras |
| 2010/0168546 A1 | 7/2010 | Kamath |
| 2010/0213127 A1 | 8/2010 | Castellarnau |
| 2010/0217181 A1 | 8/2010 | Roberts |
| 2010/0224492 A1 | 9/2010 | Ding |
| 2010/0234795 A1 | 9/2010 | Wallenas |
| 2010/0241045 A1 | 9/2010 | Kelly |
| 2010/0252490 A1 | 10/2010 | Fulkerson |
| 2010/0312172 A1 | 12/2010 | Hoffman |
| 2010/0312174 A1 | 12/2010 | Hoffman |
| 2010/0314314 A1 | 12/2010 | Ding |
| 2010/0326911 A1 | 12/2010 | Rosenbaum |
| 2011/0009798 A1 | 1/2011 | Kelly |
| 2011/0017665 A1 | 1/2011 | Updyke |
| 2011/0048949 A1 | 3/2011 | Ding et al. |
| 2011/0066043 A1 | 3/2011 | Banet |
| 2011/0077574 A1 | 3/2011 | Sigg |
| 2011/0079558 A1 | 4/2011 | Raimann |
| 2011/0087187 A1 | 4/2011 | Beck |
| 2011/0130666 A1 | 6/2011 | Dong |
| 2011/0163034 A1 | 7/2011 | Castellarnau |
| 2011/0171713 A1 | 7/2011 | Biuchel |
| 2011/0184340 A1 | 7/2011 | Tan |
| 2011/0220562 A1 | 9/2011 | Beiriger |
| 2011/0247973 A1 | 10/2011 | Sargand |
| 2011/0272337 A1 | 11/2011 | Palmer |
| 2011/0272352 A1 | 11/2011 | Braig |
| 2011/0297593 A1 | 12/2011 | Kelly |
| 2011/0315611 A1 | 12/2011 | Fulkerson |
| 2011/0315632 A1 | 12/2011 | Freije |
| 2012/0016228 A1 | 1/2012 | Kroh |
| 2012/0018377 A1 | 1/2012 | Tsukamoto |
| 2012/0083729 A1 | 4/2012 | Childers |
| 2012/0085707 A1 | 4/2012 | Beiriger |
| 2012/0092025 A1 | 4/2012 | Volker |
| 2012/0095402 A1 | 4/2012 | Lande |
| 2012/0115248 A1 | 5/2012 | Ansyln |
| 2012/0220528 A1 | 8/2012 | VanAntwerp |
| 2012/0248017 A1 | 10/2012 | Beiriger |
| 2012/0258545 A1 | 10/2012 | Ash |
| 2012/0258546 A1 | 10/2012 | Marran |
| 2012/0273354 A1 | 11/2012 | Orhan et al. |
| 2012/0273415 A1 | 11/2012 | Gerber |
| 2012/0273420 A1 | 11/2012 | Gerber |
| 2012/0277546 A1 | 11/2012 | Soykan |
| 2012/0277552 A1 | 11/2012 | Gerber |
| 2012/0277604 A1 | 11/2012 | Gerber |
| 2012/0277650 A1 | 11/2012 | Gerber |
| 2012/0277655 A1 | 11/2012 | Gerber |

(56) References Cited

U.S. PATENT DOCUMENTS

| | | |
|---|---|---|
| 2012/0277722 A1 | 11/2012 | Gerber |
| 2012/0303079 A1 | 11/2012 | Mahajan |
| 2013/0006128 A1 | 1/2013 | Olde et al. |
| 2013/0018095 A1 | 1/2013 | Vath |
| 2013/0019179 A1 | 1/2013 | Zhao |
| 2013/0020237 A1 | 1/2013 | Wilt et al. |
| 2013/0023812 A1 | 1/2013 | Hasegawa et al. |
| 2013/0025357 A1 | 1/2013 | Noack et al. |
| 2013/0027214 A1 | 1/2013 | Eng |
| 2013/0028809 A1 | 1/2013 | Barton |
| 2013/0030347 A1 | 1/2013 | Sugioka |
| 2013/0030348 A1 | 1/2013 | Lauer |
| 2013/0030356 A1 | 1/2013 | Ding |
| 2013/0037142 A1 | 2/2013 | Farrell |
| 2013/0037465 A1 | 2/2013 | Heyes |
| 2013/0056418 A1 | 3/2013 | Kopperschmidt et al. |
| 2013/0072895 A1 | 3/2013 | Kreischer et al. |
| 2013/0075314 A1 | 3/2013 | Nikolic |
| 2013/0087210 A1 | 4/2013 | Brandl et al. |
| 2013/0110028 A1 | 5/2013 | Bachmann et al. |
| 2013/0116578 A1 | 5/2013 | An |
| 2013/0199998 A1 | 8/2013 | Kelly |
| 2013/0213890 A1 | 8/2013 | Kelly |
| 2013/0213891 A1 | 8/2013 | Karoor |
| 2013/0228516 A1 | 9/2013 | Jonsson |
| 2013/0274642 A1 | 10/2013 | Soykan |
| 2013/0324915 A1 | 12/2013 | (Krensky)Britton |
| 2013/0330208 A1 | 12/2013 | Ly |
| 2013/0331774 A1 | 12/2013 | Farrell |
| 2014/0001112 A1 | 1/2014 | Karoor |
| 2014/0018728 A1 | 1/2014 | Plahey |
| 2014/0042092 A1 | 2/2014 | Akonur |
| 2014/0065950 A1 | 3/2014 | Mendelsohn |
| 2014/0088442 A1 | 3/2014 | Soykan |
| 2014/0110340 A1 | 4/2014 | White |
| 2014/0110341 A1 | 4/2014 | White |
| 2014/0138294 A1 | 5/2014 | Fulkerson |
| 2014/0158538 A1 | 6/2014 | Collier |
| 2014/0158588 A1 | 6/2014 | Pudil |
| 2014/0158623 A1 | 6/2014 | Pudil |
| 2014/0190876 A1 | 7/2014 | Meyer |
| 2014/0190885 A1 | 7/2014 | Meyer |
| 2014/0190886 A1 | 7/2014 | Pudil |
| 2014/0190891 A1 | 7/2014 | Lura |
| 2014/0217028 A1 | 8/2014 | Pudil |
| 2014/0217030 A1 | 8/2014 | Meyer |
| 2014/0220699 A1 | 8/2014 | Pudil |
| 2014/0251908 A1 | 9/2014 | Ding |
| 2014/0262812 A1 | 9/2014 | Longhenry |
| 2014/0326671 A1 | 11/2014 | Kelly |
| 2014/0336568 A1 | 11/2014 | Wong |
| 2015/0057602 A1 | 2/2015 | Mason |
| 2015/0108069 A1 | 4/2015 | Merchant |
| 2015/0108609 A1 | 4/2015 | Kushida |
| 2015/0114891 A1 | 4/2015 | Meyer |
| 2015/0144539 A1 | 5/2015 | Pudil |
| 2015/0144542 A1 | 5/2015 | Pudil |
| 2015/0157960 A1 | 6/2015 | Pudil |
| 2015/0238673 A1 | 8/2015 | Gerber |
| 2015/0250937 A1 | 9/2015 | Pudil |
| 2015/0251161 A1 | 9/2015 | Pudil |
| 2015/0251162 A1 | 9/2015 | Pudil |
| 2015/0258266 A1 | 9/2015 | Merchant |
| 2015/0306292 A1 | 10/2015 | Pudil |
| 2015/0367051 A1 | 12/2015 | Gerber |
| 2015/0367052 A1 | 12/2015 | Gerber |
| 2015/0367055 A1 | 12/2015 | Pudil |
| 2015/0367056 A1 | 12/2015 | Gerber |
| 2015/0367057 A1 | 12/2015 | Gerber |
| 2015/0367058 A1 | 12/2015 | Gerber |
| 2015/0367059 A1 | 12/2015 | Gerber |
| 2015/0367060 A1 | 12/2015 | Gerber |
| 2016/0236188 A1 | 8/2016 | Menon |
| 2016/0243299 A1 | 8/2016 | Gerber |
| 2016/0243540 A1 | 8/2016 | Menon |
| 2016/0243541 A1 | 8/2016 | Menon |
| 2017/0087533 A1 | 3/2017 | Hobot |
| 2018/0221852 A1 | 8/2018 | Pudil |

FOREIGN PATENT DOCUMENTS

| | | |
|---|---|---|
| CN | 102762268 | 10/2012 |
| CN | 103402563 A | 11/2013 |
| CN | 104936633 | 9/2015 |
| CN | 105992599 | 5/2016 |
| CN | 105658326 A | 6/2016 |
| CN | 106413878 A | 2/2017 |
| DE | 3110128 A1 | 9/1982 |
| DE | 102011052188 | 1/2013 |
| EP | 266795 A2 | 11/1987 |
| EP | 0264695 | 4/1988 |
| EP | 0614081 A1 | 10/1993 |
| EP | 0614081 B1 | 7/2000 |
| EP | 711182 B1 | 6/2003 |
| EP | 1364666 A1 | 11/2003 |
| EP | 0906768 B1 | 2/2004 |
| EP | 1701752 A2 | 9/2006 |
| EP | 1450879 | 10/2008 |
| EP | 1991289 | 11/2008 |
| EP | 1592494 B1 | 6/2009 |
| EP | 2100553 A1 | 9/2009 |
| EP | 2575827 A2 | 12/2010 |
| EP | 2576453 A2 | 12/2011 |
| EP | 2446908 | 5/2012 |
| EP | 2701580 | 11/2012 |
| EP | 2701595 | 11/2012 |
| EP | 1545652 B1 | 1/2013 |
| EP | 1684625 B1 | 1/2013 |
| EP | 2142234 B1 | 1/2013 |
| EP | 2550984 A1 | 1/2013 |
| EP | 1345856 B1 | 3/2013 |
| EP | 1938849 B1 | 3/2013 |
| EP | 2219703 B1 | 3/2013 |
| EP | 2564884 A1 | 3/2013 |
| EP | 2564885 A1 | 3/2013 |
| EP | 2344220 B1 | 4/2013 |
| EP | 1345687 | 6/2013 |
| EP | 2701596 | 3/2014 |
| EP | 2950836 | 12/2015 |
| EP | 3546042 | 10/2019 |
| EP | 3626280 | 3/2020 |
| JP | S5070281 A | 6/1975 |
| JP | S51-55193 | 5/1976 |
| JP | S51-131393 | 11/1976 |
| JP | S61164562 | 7/1986 |
| JP | 2981573 | 11/1999 |
| JP | 2005511250 | 4/2005 |
| JP | H4-90963 | 5/2005 |
| JP | 2007-44602 A | 2/2007 |
| JP | 200744602 | 2/2007 |
| JP | 200744602 A | 2/2007 |
| JP | 5099464 | 10/2012 |
| JP | 2013502987 | 10/2013 |
| WO | 9106326 A1 | 5/1991 |
| WO | 953201 A1 | 11/1995 |
| WO | 9937342 | 7/1999 |
| WO | 2000038591 A2 | 7/2000 |
| WO | 0057935 | 10/2000 |
| WO | 200066197 A1 | 11/2000 |
| WO | 200170307 A1 | 9/2001 |
| WO | 2001085295 A2 | 9/2001 |
| WO | 0185295 A2 | 11/2001 |
| WO | 2002043859 | 6/2002 |
| WO | 2003043677 A2 | 5/2003 |
| WO | 2003043680 | 5/2003 |
| WO | WO 2003041764 | 5/2003 |
| WO | 2003051422 A2 | 6/2003 |
| WO | 2004008826 | 1/2004 |
| WO | 2004009156 | 1/2004 |
| WO | 2004030716 A2 | 4/2004 |
| WO | 2004030717 A2 | 4/2004 |
| WO | 2004064616 A2 | 8/2004 |
| WO | 2004062710 A3 | 10/2004 |
| WO | WO 2005/062973 A3 | 7/2005 |

(56) References Cited

FOREIGN PATENT DOCUMENTS

| WO | 2005123230 | | 12/2005 |
|---|---|---|---|
| WO | 2005123230 | A2 | 12/2005 |
| WO | 2007089855 | A2 | 8/2007 |
| WO | WO 20070103411 | | 9/2007 |
| WO | 2008075951 | A1 | 6/2008 |
| WO | 2009026603 | | 12/2008 |
| WO | 2009026603 | A1 | 3/2009 |
| WO | 2009064984 | | 5/2009 |
| WO | 2009157877 | A1 | 12/2009 |
| WO | 2009157878 | A1 | 12/2009 |
| WO | 20090157877 | | 12/2009 |
| WO | 2010028860 | | 3/2010 |
| WO | 2010028860 | A1 | 3/2010 |
| WO | 2010102190 | A4 | 11/2010 |
| WO | 2010141949 | | 12/2010 |
| WO | WO 2011/017215 | | 2/2011 |
| WO | 2011025705 | A1 | 3/2011 |
| WO | 2012148781 | | 11/2012 |
| WO | 2012148786 | | 11/2012 |
| WO | 2012148789 | | 11/2012 |
| WO | 2012162515 | A2 | 11/2012 |
| WO | 20120277551 | | 11/2012 |
| WO | 2012172398 | | 12/2012 |
| WO | 2013019179 | | 2/2013 |
| WO | 2013019179 | A1 | 2/2013 |
| WO | 2013019994 | A2 | 2/2013 |
| WO | 2013022024 | A1 | 2/2013 |
| WO | 2013022837 | A1 | 2/2013 |
| WO | 2013025844 | | 2/2013 |
| WO | 2013025957 | | 2/2013 |
| WO | 2013027214 | | 2/2013 |
| WO | 2013028809 | | 2/2013 |
| WO | 2013028809 | A3 | 2/2013 |
| WO | WO 2013/019179 | | 2/2013 |
| WO | WO 2013/019994 | | 2/2013 |
| WO | WO 2013-025957 | | 2/2013 |
| WO | WO 2013-028809 | | 2/2013 |
| WO | WO 2013/028809 | | 2/2013 |
| WO | WO 2013019179 | | 2/2013 |
| WO | WO2014121238 | A1 | 2/2013 |
| WO | 2013030642 | A1 | 3/2013 |
| WO | 2013030643 | A1 | 3/2013 |
| WO | 2013019994 | A3 | 4/2013 |
| WO | 2012060700 | | 5/2013 |
| WO | 2012162515 | A3 | 5/2013 |
| WO | 2013025844 | A3 | 5/2013 |
| WO | 2013101888 | | 7/2013 |
| WO | 2013103607 | A1 | 7/2013 |
| WO | 2013103906 | | 7/2013 |
| WO | WO 2013/103607 | | 7/2013 |
| WO | WO 2013109922 | | 7/2013 |
| WO | 2013114063 | A1 | 8/2013 |
| WO | 2013121162 | A1 | 8/2013 |
| WO | 14066254 | | 5/2014 |
| WO | 14066255 | | 5/2014 |
| WO | 14077082 | | 5/2014 |
| WO | 2014121162 | | 8/2014 |
| WO | 2014121163 | | 8/2014 |
| WO | 2014121167 | | 8/2014 |
| WO | 2014121169 | | 8/2014 |
| WO | 2015060914 | | 4/2015 |
| WO | WO 2015/080895 | | 4/2015 |
| WO | WO 2015060914 | | 4/2015 |
| WO | WO 2015/126879 | | 8/2015 |
| WO | 2015142624 | | 9/2015 |
| WO | 2015199764 | | 12/2015 |
| WO | 2015199765 | | 12/2015 |
| WO | 2015199863 | | 12/2015 |
| WO | 2015199864 | | 12/2015 |
| WO | WO 2015-199863 | | 12/2015 |
| WO | WO 2015-199864 | | 12/2015 |
| WO | WO 2015199765 | | 12/2015 |
| WO | WO 2016/191039 | | 12/2016 |
| WO | WO 2016/191041 | | 12/2016 |

OTHER PUBLICATIONS

[NPL105] Brynda, et. al., The detection of toman 2-microglobuiin by grating coupler immunosensor with three dimensional antibody networks. Biosensors & Bioelectronics, 1999, 363-368,14(4).

[NPL10] Wheaton, et al., Dowex Ion Exchange Resins-Fundamentals of Ion Exchange; Jun. 2000, pp. 1-9. http://www.dow.com/scripts/litorder.asp?filepath=liquidseps/pdfs/noreg/177-01837.pdf.

[NPL111] Zhong, et. al., Miniature urea sensor based on H(+)-ion sensitive field effect transistor and its application in clinical analysis, Chin. J. Biotechnol., 1992, 57-65.8(1).

[NPL119] PCT/US2012/034331, International Search Report and Written Opinion dated Jul. 9, 2012.

[NPL121] Roberts M, The regenerative dialysis (REDY) sorbent system. Nephrology, 1998, 275-278:4.

[NPL138] U.S. Appl. No. 61/480,544.

[NPL139] U.S. Appl. No. 61/480,541 dated Apr. 29, 2011.

[NPL142] Hemametrics, Crit-Line Hematocrit Accuracy, 2003,1-5, vol. 1, Tech Note No. 11 (Rev. D).

[NPL144] Weissman, S., et al., Hydroxyurea-induced hepatitis in human immunodeficiency virus-positive patients. Clin. Infec. Dis, (Jul. 29, 1999): 223-224.

[NPL146] PCT/US2012/034334, International Search Report, dated Jul. 6, 2012.

[NPL147] PCT/US2012/034335, International Search Report, dated Sep. 5, 2012.

[NPL148] PCT/US/2012/034327, International Search Report, dated Aug. 13, 2013.

[NPL149] PCT/US/2012/034329, International Search Report, dated Dec. 3, 2012.

[NPL162] International Search Report from PCT/US2012/051946 dated Mar. 4, 2013.

[NPL163] U.S. Appl. No. 61/526,209.

[NPL169] Wang, Fundamentals of intrathoracic impedance monitoring in heart failure, Am. J. Cardiology, 2007, 3G-10G: Suppl.

[NPL16] PCT/US2014/067650 International Search Report Written Opinion dated Mar. 9, 2015.

[NPL176] Bleyer, et al., Sudden and cardiac death rated in hemodialysis patients, Kidney International. 1999,1553-1559: 55.

[NPL187] PCT/US2012/034333, International Preliminary Report on Patentability, dated Oct. 29, 2013.

[NPL188] PCT/US2012/034333, International Search Report, dated Aug. 29, 2012.

[NPL188] PCT/US2012/034333, International Search Report, dated Aug. 29, 2013.

[NPL197] PCT/US2012/034330, International Preliminary Report on Patentability, dated Oct. 29, 2013.

[NPL1] PCT/US2014/065950 International Search Report and Written Opinion dated Feb. 24, 2015.

[NPL205] Culleton, BF et al. Effect of Frequent Nocturnal Hemodialysis vs. Conventional Hemodialysis on Left Ventricular Mass and Quality of Life. 2007 Journal of the American Medical Association 298 (11), 1291-1299.

[NPL217] U.S. Appl. No. 13/757,722, filed Feb. 1, 2013.

[NPL218] U.S. Appl. No. 13/757,794, filed Feb. 2, 2012.

[NPL219] U.S. Appl. No. 13/791,755, filed Mar. 8, 2013.

[NPL21] U.S. Appl. No. 13/424,479 dated Nov. 1, 2012.

[NPL220] U.S. Appl. No. 13/757,792, filed Feb. 2, 2013.

[NPL222] U.S. Appl. No. 13/757,794, filed Feb. 2, 2013.

[NPL227] U.S. Appl. No. 13/837,287, filed Mar. 15, 2013.

[NPL22] U.S. Appl. No. 13/424,429 dated Nov. 1, 2012.

[NPL230] Redfield, et. al., Restoration of renal response to atria! natriuretic factor in experimental low-output heat failure, Am. J. Physiol., Oct. 1, 1989, R917-923:257.

[NPL231] Rogoza, et. al., Validation of A&D UA-767 device for the self-measurement of blood pressure, Blood Pressure Monitoring, 2000, 227-231, 5(4).

[NPL234] Lima, et. al., An electrochemical sensor based on nanostructure hollsndite-type manganese oxide for detection of potassium ion, Sensors, Aug. 24, 2009, 6613-8625, 9.

[NPL235] MacLean, et. al., Effects of hindlimb contraction on pressor and muscle interstitial metabolite responses in the cat, J. App. Physiol., 1998, 1583-1592, 85(4).

(56) References Cited

OTHER PUBLICATIONS

[NPL237] U.S. Appl. No. 13/757,693, dated Feb. 1, 2013.
[NPL238] PCT Application, PCT/US20013/020404, filed Jan. 4, 2013.
[NPL23] U.S. Appl. No. 13/424,525.
[NPL240] U.S. Appl. No. 13/836,973, filed Mar. 15, 2013.
[NPL241] U.S. Appl. No. 14/259,655, filed Apr. 23, 2014.
[NPL242] U.S. Appl. No. 14/259,589, filed Apr. 23, 2014.
[NPL243] U.S. Appl. No. 13/757,693, filed Jan. 4, 2013.
[NPL244] U.S. Appl. No. 13/836,079, filed Mar. 15, 2013.
[NPL245] U.S. Appl. No. 14/240,129, filed Aug. 22, 2013.
[NPL246] PCT/US2014/014346 International Search Report and Written Opinion.
[NPL247] U.S. Appl. No. 13/835,735, filed Mar. 15, 2013.
[NPL248] PCT/US2014/014345 International Search Report and Written Opinion, dated May 2014.
[NPL250] U.S. Appl. No. 13/835,735 IDS, filed Jun. 13, 2013.
[NPL264] PCT/US2014/014357 International Search Report and Written Opinion dated May 19, 2014.
[NPL268] Ronco et al. 2008, Cardiorenal Syndrome, Journal American College Cardiology, 52:1527-1539, Abstract.
[NPL26] Overgaard, et. al., Activity-induced recovery of excitability in K+-depressed rat soleus muscle, Am. J. P 280: R48-R55, Jan. 1, 2001.
[NPL27] Overgaard et. al., Relations between excitability and contractility in rate soleus muscle: role of the NA+-K+ pump and NA+-K-S gradients. Journal of Physiology, 1999, 215-225, 518(1).
[NPL2] PCT/US2015/032492 International Search Report dated Nov. 19, 2015.
[NPL306] Coast, et al. 1990, An approach to Cardiac Arrhythmia analysis Using Hidden Markov Models, IEEE Transactions on Biomedical Engineering. 1990, 37(9):826-835.
[NPL310] U.S. Appl. No. 61/480,532.
[NPL317] U.S. Appl. No. 61/480,530.
[NPL318] U.S. Appl. No. 61/480,528 dated Apr. 29, 2011.
[NPL32] Secemsky, et. al., High prevalence of cardiac autonomic dysfunction and T-wave alternans in dialysis patients. Heart Rhythm, Apr. 2011,592-598: vol. 8, No. 4.
[NPL35] Wei, et. al., Fullerene-cryptand coated piezoelectric crystal urea sensor based on urease, Analytica Chimica Acta, 2001,77-85:437.
[NPL376] Gambro AK 96 Dialysis Machine Operators Manual, Dec. 2012. p. 1-140.
[NPL376] Gambro AK 96 Dialysis Machine Operators Manual, Dec. 2012. p. 141-280.
[NPL376] Gambro AK 96 Dialysis Machine Operators Manual, Dec. 2012. p. 281-420.
[NPL376] Gambro AK 96 Dialysis Machine Operators Manual, Dec. 2012. p. 421-534.
[NPL37] U.S. Appl. No. 13/368,225 dated Feb. 7, 2012.
[NPL383] Leifer et al., A Study on the Temperature Variation of Rise Velocity for Large Clean Bubbles, J. Atmospheric & Oceanic Tech., vol. 17, pp. 1392-1402, Oct. 2000.
[NPL384] Talaia, Terminal Velocity of a Bubble Rise in a Liquid Column, World Acad. of Sci., Engineering & Tech., vol. 28, pp. 264-268, Published Jan. 1, 2007.
[NPL386] The FHN Trial Group. In-Center. Hemodialysis Six Times per Week versus Three Times per Week, New England Journal of Medicine, 2010 Abstract.
[NPL387] Gotch FS, Sargent JA A mechanistic analysis of the National Cooperative Dialysis Study (NCDS). Kidney int. 1985: 28:526-34.
[NPL388] Daugirdas JT. Second generation logarithmic estimates of single-pool variable volume Kt/V and analysis of error. J Am Soc Nephrol, 1993: 4:1205-13.
[NPL389] Steil et al. Intl Journ Artif Organs, 1993, In Vivo Verification of an Automatic Noninvasive System for Real Time Kt Evaluation, ASAIO J., 1993, 39:M348-52.
[NPL39] PCT/US2012/034332, International Search Report, dated Jul. 5, 2012.
[NPL3] PCT/US2015/019901 International Search Report and Written Opinion dated Jun. 5, 2015.
[NPL46] Siegenthaler, et al., Pulmonary fluid status monitoring with intrathoracic impedance, Journal of Clinical Monitoring and Computing, 24:449-451, published Jan. 12, 2011.
[NPL47] U.S. Appl. No. 61/480,544.
[NPL494] John Wm Agar: Review: Understanding sorbent dialysis systems, NEPHROLOGY, vol. 15, No. 4, Jun. 1, 2010, pp. 406-411.
[NPL499] EP. App. 14746193.3 Search Report dated Oct. 19, 2016.
[NPL4] PCT/US2015/016270 International Search Report and Written Opinion dated Jun. 5, 2015.
[NPL518] Office Action in U.S. Appl. No. 14/269,589, dated Nov. 4, 2016.
[NPL519] Office Action in U.S. Appl. No. 13/586,824 dated Dec. 21, 2015.
[NPL520] Office Action in U.S. Appl. No. 13/586,824 dated Jun. 4, 2015.
[NPL532] Eureopean Search Report for App. No. EP14745643 dated Oct. 6, 2016.
[NPL534] Office Action in U.S. Appl. No. 13/586,824 dated Dec. 21, 2015.
[NPL548] PCT/US15/18587 International Preliminary Report on Patentability dated Jun. 6, 2016.
[NPL550] European Search Opinion for App. No. EP12826180 dated Mar. 19, 2015.
[NPL551] European Search Opinion for App. No. EP12826180 dated Jan. 18, 2016.
[NPL552] Khanna, Ramesh, R.T. Krediet, and Karl D. Nolph. Nolph and Gokals Textbook of Peritoneal Dialysis New York: Springer 2009. Print.
[NPL553] Ruperez et al., Comparison of a tubular pulsatile pump and a volumetric pump for continuous venovenous renal replacement therapy in a pediatric animal model, 51 ASAIO J. 372, 372-375 (2005).
[NPL554] St. Peter et al., Liver and kidney preservation by perfusion, 359 The Lancet 604, 606(2002).
[NPL555] Dasselaar et al., Measurement of relative blood volume changes during hemodialysis: merits and limitations, 20 Nephrol Dial Transpl. 2043, 2043-2044 (2005).
[NPL556] Ralph T. Yang, Adsorbents: Fundamentals and Applications 109 (2003).
[NPL557] Henny H. Billett, Hemoglobin and Hematocrit, in Clinical Methods: The History, Physical, and Laboratory Examinations 719(HK Walker, WD Hall, & JW Hurst ed., 1990).
[NPL558] Office Action in U.S. Appl. No. 13/565,733 dated Jan. 11, 2016.
[NPL559] Office Action in U.S. Appl. No. 13/565,733 dated Jun. 11, 2015.
[NPL55] U.S. Appl. No. 13/424,454.
[NPL560] Office Action in U.S. Appl. No. 13/586,824 dated Jun. 4, 2015.
[NPL561] Office Action in U.S. Appl. No. 13/757,792 dated Jun. 2, 2016.
[NPL562] Office Action in U.S. Appl. No. 13/757,796 dated Apr. 13, 2015.
[NPL563] Office Action in U.S. Appl. No. 13/757,796 dated Dec. 21, 2015.
[NPL564] Office Action in U.S. Appl. No. 13/835,735 dated Oct. 13, 2015.
[NPL565] Office Action in U.S. Appl. No. 13/836,079 dated Apr. 17, 2015.
[NPL566] Office Action in U.S. Appl. No. 13/836,079 dated Jun. 30, 2016.
[NPL569] Office Action in U.S. Appl. No. 13/791,755 dated Mar. 16, 2016.
[NPL570] Office Action in U.S. Appl. No. 13/791,755 dated Aug. 9, 2016.
[NPL571] Office Action in U.S. Appl. No. 13/835,735 dated Jun. 16, 2016.
[NPL572] Office Action in U.S. Appl. No. 13/836,079 dated Nov. 6, 2015.
[NPL57] U.S. Appl. No. 13/424,467.

(56) References Cited

OTHER PUBLICATIONS

[NPL584] Office Action in App. No. AU 2015280604 dated Apr. 8, 2016.
[NPL586] International Search Report from International Application No. PCT/US2014/014347 dated May 9, 2014.
[NPL590] PCT/US2016/030319 Written Opinion dated Jul. 27, 2016.
[NPL591] PCT/US2016/030320 Written Opinion dated Jul. 27, 2016.
[NPL596] PCT/US2012/014347, International Search Report.
[NPL5] PCT/US2015/016273 International Search Report and Written Opinion dated Jun. 9, 2015.
[NPL601] Wester et al., A regenerable postassium and phosphate sorbent system to enhance dialysis efficacy and device portability: an in vitro study Nephrol Dial Transplant (2013) 28: 2364-2371 Jul. 3, 2013.
[NPL602] Office Action in App. No. JP 2016-515476 dated Dec. 26, 2016.
[NPL603] Japanese Patent Publication No. S50-70281A.
[NPL605] PCT/US2015/032494 Written Opinion dated Nov. 19, 2015.
[NPL606] PCT/US2015/032494 International Search Report dated Nov. 19, 2015.
[NPL607] PCT/US2015/019901 International Preliminary Report on Patentability dated May 27, 2016.
[NPL608] PCT/US2015/019901 Written Opinion dated May 27, 2016.
[NPL609] PCT/US2015/019901 Written Opinion dated Jun. 5, 2015.
[NPL610] PCT/US2015/019901 International Search Report dated Jun. 5, 2015.
[NPL611] PCT/US2015/032485 International Preliminary Report on Patentability dated May 11, 2016.
[NPL612] PCT/US2015/032485 International Preliminary Report on Patentability dated May 11, 2016.
[NPL613] PCT/US20115/032485 International Preliminary Reporton Patentability dated May 11, 2016.
[NPL614] PCT/US2016/030304 International Search Report dated Jul. 27, 2016.
[NPL615] PCT/US2016/030304 Written Opinion dated Jul. 27, 2016.
[NPL616] PCT/US2016/030312 Written Opinion dated Jul. 28, 2016.
[NPL617] PCT/US2016/030312 International Search Report dated Jul. 28, 2016.
[NPL618] PCT/US2016/030319 International Search Report dated Jul. 27, 2016.
[NPL619] PCT/US2016/030319 Written Opinion dated Jul. 27, 2016.
[NPL620] PCT/US2016/030320 Written Opinion dated Jul. 28, 2016.
[NPL621] PCT/US2016/030320 International Search Report dated Jul. 28, 2016.
[NPL622] PCT/US2015/032485 Written Opinion dated Oct. 16, 2015.
[NPL623] PCT/US2015/032485 Written Opinion dated Oct. 16, 2016.
[NPL626] PCT/US2015/032485 International Search Report and Written Opinion dated Oct. 16, 2015.
[NPL62] U.S. Appl. No. 13/424,533.
[NPL634] PCT/US2016/030320 International Preliminary Report on Patentability, dated Apr. 20, 2017.
[NPL654] International Preliminary Report from International Application No. PCT/US2014/014348 dated Jan. 9, 2015.
[NPL655] European Search Report from European Application No. EP 14746193.3 dated Oct. 19, 2016.
[NPL656] European Search Report from European Application No. EP 14746193.3 dated Jun. 8, 2016.
[NPL657] PCT/US2014/014345 Written Opinion dated Jun. 24, 2015.
[NPL658] PCT/US2014/014345 International Search Report and Written Opinion dated May 30, 2014.
[NPL659] Office Action in European Application No. 14746428.03 dated Feb. 8, 2017.
[NPL660] European Search Report in European Application No. 14746428.03 dated Aug. 25, 2016.
[NPL661] PCT/US2014/014346 Writtent Opinion dated Apr. 10, 2015.
[NPL662] PCT/US2014/014346 International Search Report and Writtent Opinion dated May 23, 2014.
[NPL663] Ep 14746415.0 European Search Report dated Aug. 22, 2016.
[NPL664] Office Action in European Application No. EP 14746415.0 dated Apr. 19, 2017.
[NPL670] Office Action in European Application No. 14746415.0 dated Apr. 19, 2017.
[NPL67] U.S. Appl. No. 13/424,490.
[NPL681] PCT/US2015/020047 International Search Report and Written Opinion dated Jun. 29, 2015.
[NPL682] PCT/US2015/020047 International Preliminary Report on Patentability dated Jun. 30, 2015.
[NPL684] PCT/US2015/020044 Written Opinion dated Jun. 21, 2016.
[NPL685] PCT/US2015/020044 International Preliminary Report on Patentability dated Nov. 4, 2016.
[NPL686] PCT/US2015/020044 International Search Report dated Jun. 30, 2015.
[NPL688] US2015/019881 Written Opinion dated Jun. 16, 2016.
[NPL689] US2015/019881 Written Opinion dated May 9, 2016.
[NPL68] U.S. Appl. No. 13/424,517.
[NPL690] US2015/019881 International Search Report and Written Opinion dated Jun. 29, 2015.
[NPL692] PCT/US2014/065950 International Preliminary Report on Patentability dated Oct. 28, 2015.
[NPL696] PCT/US2015/032485 Written Opinion dated May 9, 2016.
[NPL6] PCT/US2015/032492 Written Opinion dated Nov. 19, 2015.
[NPL720] PCT/US2015/019901 International Search Report and Written Opinion dated Jun. 5, 2015.
[NPL721] PCT/US2015/019901 International Preliminary Report on Patentability dated May 27, 2016.
[NPL722] PCT/US2015/032494 International Preliminary Report on Patentablity dated Dec. 27, 2016.
[NPL730] Office Action for Chinese Application No. 201580009562.5 dated Jul. 3, 2017.
[NPL734] International Preliminary Report on Patentability for Application No. PCT/US2015/032492 dated Jun. 30, 2017.
[NPL736] Office Action in European Application No. 14746193.3 dated Apr. 19, 2017.
[NPL737] International Preliminary Report on Patentability for Application No. PCT/US2015/016273 dated Feb. 19, 2016.
[NPL747] European Search Report for App. No. 15751391.2 dated Aug. 4, 2017.
[NPL755] European Search Report and supplementary Search Report for App. No.14865374.4 dated Jun. 12, 2017.
[NPL756] European Search Report and Supplemental Search Report in European Application No. 14865374.4 dated Jun. 12, 2017.
[NPL7] PCT/US2015/020046 International Search Report and Written Opinion dated Jun. 29, 2015.
[NPL81] U.S. Appl. No. 61/480,539 dated Apr. 29, 2011.
[NPL84] U.S. Appl. No. 61/480,535 dated Apr. 29, 2011.
[NPL8] PCT/US2015/020044 International Search Report Written Opinion dated Jun. 30, 2015.
[NPL90] Nedelkov, et. al., Design of buffer exchange surfaces and sensor chips for biosensor chip mass spectrometry, Proteomics, 2002, 441-446, 2(4).
[NPL] European Search Report App 14865374.4, Jun. 12, 2017.
Chinese Office Action in App. No. 201580009563.X, dated Mar. 13, 2018.
European Search Report for App. No. 15812081.6, dated Mar. 8, 2018.
European Search Report for App. No. 18153940.4, dated Jun. 12, 2018.

(56) References Cited

OTHER PUBLICATIONS

European Search Report for App. No. 18153940.4, dated Sep. 28, 2018.
European Search Report for App. No. 19191469.6, dated Jan. 8, 2020.
European Search Report for EP 15811439, dated Feb. 15, 2018.
European Search Report for EP App. No. 15810804.3, dated Feb. 15, 2018.
European Search Report for EP App. No. 15811326.6, dated Feb. 14, 2018.
European Search Report for EP App. No. 15811573.3, dated Feb. 15, 2018.
European Search Report for EP App. No. 15812413.1, dated Feb. 2, 2018.
European Search Report for EP18177673.3-1104 (dated Oct. 19, 2018).
European Search Report for EP18177683.2-1104 (dated Nov. 8, 2018).
European Search Report in EP 15811454, dated Feb. 15, 2018.
European Search Report in EP 15812559.1, dated Jan. 31, 2018.
Office Action for Chinese App. No. 201711179516.7, dated Sep. 11, 2019.
Office Action for Chinese App. No. 201810042927, dated Sep. 23, 2019.
Office Action for European App. No. 17203968.7, dated Nov. 14, 2019.
Office Action in Japanese Application No. 2016-553344, dated Apr. 24, 2018.
PCT/US2016/030304_IPRP.
PCT/US2016/030319_IPRP.
Search Report for EP App. No. 17203984.4, dated Mar. 29, 2018.
Search Report for European App. No. 19187736.4, dated Dec. 16, 2019.
Search Report in EP App. No. 15752771, dated Nov. 22, 2017.
European Search Report for App. No. 19197167.0, dated Jan. 30, 2020.
European Search Report for App. No. 20164524.9, dated Aug. 21, 2020.
Chinese Office Action for App. No. 201810580243.5, dated Jul. 3, 2020.
European Search Report for App. No. 20158130.3, dated Jul. 8, 2020.

RECHARGE SOLUTION FOR ZIRCONIUM PHOSPHATE

CROSS-REFERENCE TO RELATED APPLICATION

This application claims benefit of and priority to Indian Patent Application Serial No. 201841031852 filed Aug. 24, 2018, the disclosure of the above-identified application is hereby incorporated by reference in its entirety.

FIELD OF THE INVENTION

The invention relates to devices, systems, and methods that can generate a required recharge solution for recharging and disinfecting zirconium phosphate by introducing recharging constituent components through a recharging device. Reusable sorbent modules can contain the zirconium phosphate to be recharged. The systems and methods include mixing one or more solutions to generate the recharge solution having specified concentrations of sodium and acid for recharging and disinfecting the zirconium phosphate inside the reusable module.

BACKGROUND

Zirconium phosphate is used in sorbent dialysis to remove waste and unwanted solutes from dialysate, including ammonium, potassium, calcium, and magnesium cations. The zirconium phosphate is generally packed in a sorbent cartridge, which is discarded and replaced after use. The discarded sorbent cartridges are broken down and the zirconium phosphate is separated from the other sorbent materials. Because zirconium phosphate is expensive and rechargeable, sorbent re-processors treat the recovered materials with chemical solutions. The recycling process requires transporting the materials to reprocessing facilities and involves laborious recycling steps in addition to recharging the sorbent materials. Further, because the sorbent material must be re-packed into a new cartridge, the sorbent material cannot be immediately reused with several other sorbent components, for sale. Conventional methods drive up costs and infrastructure requirements and increase complexity and waste. Further, the recharge solutions used in conventional methods are generated by hand, introducing the possibility of human error.

Hence, there is a need for systems and methods of recharging zirconium phosphate within reusable sorbent modules. Hence, there is a need for a modular system wherein each module contains one sorbent component so that each component can have ideal washing components and processes specific to that particular sorbent component. The need extends to systems and methods for generating a recharge solution that can be pumped through the sorbent module to recharge the zirconium phosphate with specified concentrations of solutes in the recharge solution. The systems and methods should include methods that efficiently generate the recharge solution(s) from constituent parts, thereby reducing complexity and costs.

SUMMARY OF THE INVENTION

The first aspect of the invention relates to a system. In any embodiment, the system can comprise a sorbent recharger comprising a recharging flow path comprising at least one receiving compartment for a zirconium phosphate sorbent module; the at least one receiving compartment comprising a zirconium phosphate module inlet and a zirconium phosphate module outlet; at least one recharge solution source; the at least one recharge solution source comprising an acid source and a sodium source; and a controller controlling at least one pump to introduce fluid from the at least one recharge solution source through the zirconium phosphate sorbent module.

In any embodiment, the at least one recharge solution source can further comprise a base source. In any embodiment, the sodium source can be selected from the group consisting of sodium chloride, sodium acetate, sodium phosphate, sodium citrate, sodium hydroxide, and combinations thereof. In any embodiment, the acid source can be selected from the group consisting of acetic acid, phosphoric acid, sulfuric acid, citric acid, and combinations thereof. In any embodiment, both the sodium source and acid source can be selected from a single compound such as sodium diacetate, monosodium citrate, monosodium phosphate, sodium bisulfate, and combinations thereof.

In any embodiment, the at least one recharge solution source can comprise a source of solid sodium salt, solid acid, and/or solid sodium salt and solid acid.

In any embodiment, the source of solid sodium salt, solid acid, and/or solid sodium solid sodium salt and acid can comprise a partitioned bag containing solid sodium salt, solid acid, and/or solid sodium salt and solid acid.

In any embodiment, partitioned bag containing solid sodium salt, solid acid, and/or solid sodium salt and solid acid can comprise an inlet fluidly connectable to a water source and an outlet fluidly connectable to the recharging flow path.

In any embodiment, the at least one recharge solution source can comprise a saturated source of a sodium salt.

In any embodiment, at least one recharge solution source can comprise a saturated source of sodium acetate and acetic acid.

In any embodiment, at least one recharge solution source can comprise a liquid acid.

In any embodiment, the system can comprise a water source fluidly connected to the recharging flow path.

In any embodiment, at least one recharge solution source can comprise sodium hydroxide.

In any embodiment, the system can comprise a mixer fluidly connected or in the recharging flow path.

In any embodiment, the system can comprise at least one sensor fluidly connected or in the recharging flow path.

In any embodiment, the system can comprise a second recharging flow path comprising a second receiving compartment for a zirconium oxide sorbent module; the second receiving compartment comprising a zirconium oxide module inlet and a zirconium oxide module outlet; and at least a second recharge solution source; the at least second recharge solution source containing least a hydroxyl source and a free chlorine source.

The features disclosed as being part of the first aspect of the invention can be in the first aspect of the invention, either alone or in combination, or follow a preferred arrangement of one or more of the described elements.

The second aspect of the invention is drawn to a method. In any embodiment, the method can comprise the steps of generating a recharge solution containing sodium acid, or combinations thereof in a recharging flow path; and recharging zirconium phosphate in a zirconium phosphate sorbent module by introducing the recharge solution through the zirconium phosphate sorbent module.

In any embodiment, the step of generating the recharge solution can comprise mixing two or more saturated solutions of sodium, acid, or combinations thereof with water.

In any embodiment, at least one of the two or more saturated solutions can comprise a saturated solution of sodium chloride, sodium acetate, sodium diacetate, or combinations thereof.

In any embodiment, the method can comprise the step of generating the two or more saturated solutions by adding water to a source of solid sodium salt, solid acid, or combinations thereof.

In any embodiment, the method can comprise the step of introducing water into the recharging flow path to generate a recharge solution having specified concentrations of sodium and acid.

In any embodiment, the method can comprise the step of measuring a concentration of sodium or pH in the recharge solution.

In any embodiment, the method can comprise the step of adjusting a flow rate of at least one fluid used in generating the recharge solution if the concentration of sodium or the pH is outside of a predetermined range.

In any embodiment, the step of measuring the concentration of sodium or pH in the recharge solution can comprise using one or more conductivity sensors.

In any embodiment, the method can be carried out by the system of the first aspect of the invention.

The features disclosed as being part of the second aspect of the invention can be in the second aspect of the invention, either alone or in combination, or follow a preferred arrangement of one or more of the described elements.

DETAILED DESCRIPTION OF THE INVENTION

Figure 1A:
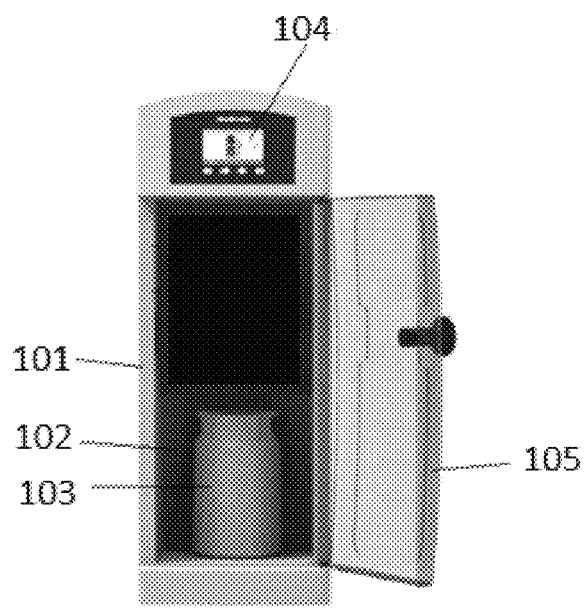
FIG. 1A shows a sorbent recharger for recharging zirconium phosphate in a sorbent module.

Unless defined otherwise, all technical and scientific terms used have the same meaning as commonly understood by one of ordinary skill in the art.

The articles "a" and "an" are used to refer to one or to over one (i.e., to at least one) of the grammatical object of the article. For example, "an element" means one element or over one element.

The term "acetic acid" refers to $CH_3CO_2H$, either in liquid, solid, or solution form.

An "acid" as used herein can be either a Lewis acid or a Brønsted-Lowry acid. A Lewis acid is a compound capable of accepting a lone pair of electrons. A Brønsted-Lowry acid is a compound capable of donating a hydrogen ion to another compound An "acid source" is a solid, fluid, or concentrate source from which an acid solution can be obtained.

The term "adding" or to "add" refers to moving a substance, liquid, gas, or combination thereof into a reservoir, containing, or flow path.

The term "adjusting" or to "adjust" refers to changing any parameter of a system or process.

A "base source" is a fluid or concentrate source from which a base solution can be obtained.

The term "citric acid" refers to $C_6H_8O_7$, either in solution or solid form.

The term "comprising" includes, but is not limited to, whatever follows the word "comprising." Use of the term indicates the listed elements are required or mandatory but that other elements are optional and may be present.

The term "concentration" refers to an amount of a first substance dissolved in a second substance. The term refers to a relative amount of a given substance contained within a solution or in a particular volume and can represent an amount of solute per unit volume of solution.

The term "conductivity sensor" refers to a device for measuring conductance, or the inverse of the electrical resistance, of a fluid or substance.

The term "consisting of" includes and is limited to whatever follows the phrase "consisting of" The phrase indicates the limited elements are required or mandatory and that no other elements may be present.

The term "consisting essentially of" includes whatever follows the term "consisting essentially of" and additional elements, structures, acts or features that do not affect the basic operation of the apparatus, structure or method described.

A "controller" can be a combination of components that act together to maintain a system to a desired set of performance specifications. The control system can use processors, memory and computer components configured to interoperate to maintain the desired performance specifications. The control system can also include fluid or gas control components, and solute control components as known within the art to maintain performance specifications.

The terms "control," "controlling," or "controls" refers to the ability of one component to direct the actions of a second component, element, or process.

The term "flow rate" refers to a volume of a fluid, gas, or combination thereof passing a specified point per unit of time.

The term "fluidly connectable" refers to the ability of providing for the passage of fluid, gas, or combination thereof, from one point to another point. The ability of providing such passage can be any connection, fastening, or forming between two points to permit the flow of fluid, gas, or combinations thereof. The two points can be within or between any one or more of compartments of any type, modules, systems, components, and rechargers.

The term "fluidly connected" refers to a particular state such that the passage of fluid, gas, or combination thereof, is provided from one point to another point. The connection state can also include an unconnected state, such that the two points are disconnected from each other to discontinue flow. It will be further understood that the two "fluidly connectable" points, as defined above, can from a "fluidly connected" state. The two points can be within or between any one or more of compartments, modules, systems, components, and rechargers, all of any type.

A "free chlorine source" refers to a substance that can generate chlorine, hypochlorite ions, or hypochlorous acid either as a gas or in solution.

The term "generate" or "generating" refer to forming a solution or substance from constituent parts.

The term "hydroxyl source" refers to a fluid, solid, or concentrate containing a substance that comprises hydroxide anions.

The term "inlet" can refer to a portion of container, flow path, or component through which fluid, gas, or a combination thereof can be drawn into the container, flow path, or component.

The terms "introducing," "introduced," or to "introduce" refers to conveying or moving a fluid, a gas, or a combination thereof by any pressure, pressure differential, force, pumping action, displacement, or other motive force known to those of skill in the art.

The term "liquid" refers to a material in the liquid form of matter. A liquid can refer to a single material, a mixture, or a solution.

The term "measuring" or to "measure" refers to determining a state or parameter of a system or substance.

A "mixer" can be a component receiving one or more fluids from one or multiple sources that can combine, associate, or otherwise bring the fluids together. The mixer may include components that agitate the fluids to facilitate bringing the one or more fluids together.

The term "mixing" or to "mix" generally refers to causing one or more fluids from any source to combine together. For example, "mixing" can include laminar or turbulent flow at a location in a fluid line or a junction. Another example of "mixing" can include receiving one or more fluids in a component configured to receive fluids from one or multiple sources and to mix the fluids together in the component. Additionally, mixing can refer to the dissolution of a solid or solids with a fluid, wherein the solid or solids is dissolved in the fluid.

The term "monosodium citrate" refers to $NaC_6H_7O_7$, either in solution or solid form.

The term "monosodium phosphate" refers to $NaH_2PO_4$, either in solution or solid form The term "outlet" can refer to a portion of container, flow path, or component through which fluid, gas, or a combination thereof can be drawn out of the container, flow path, or component.

A "partitioned bag" can be any container having an inlet and an outlet having a separator positioned inside the partitioned bag wherein the partitioned bag can have two or more partitions, compartments, or sections of defined space. For example, the partitioned bag can have a first compartment, section, or space containing a solid material, wherein liquid can be added to the first compartment, section, or space bag through an inlet positioned on one side of the separator in the first compartment, section, or space. The introduced liquid can then dissolve the solid material in the first compartment, section, or space resulting in a liquid solution. The resulting liquid solution can then flow to a second compartment, section, or space separated by, or on another side of the separator of the partitioned bag. The resulting liquid solution can then exit the second compartment, section, or space of the partitioned bag through an outlet positioned on the second compartment, section, or space.

The term "pH" refers to the inverse log of the hydrogen ion concentration in solution.

The term "phosphoric acid" refers to $H_3PO_4$, either in solution or solid form.

The term "predetermined range" can be any range of possible values for a parameter obtained in advance or a priori to actual use in a method.

The term "pump" refers to any device that causes the movement of fluids or gases by applying suction or pressure.

A "receiving compartment" can be a compartment, section, or chamber within a sorbent recharger into which a sorbent module can be positioned to be recharged.

A "recharge solution" or "recharge solutions" can be a solution containing appropriate ions for recharging a specific sorbent material. A recharge solution can be a single solution containing all necessary ions for recharging a sorbent material. Alternatively, the recharge solution can contain some of the ions for recharging the sorbent material, and one or more other recharge solutions can be used to form a composite "recharge solution" to recharge the sorbent material, as described herein.

A "recharge solution source" can be any fluid or concentrate source from which a recharge solution can be stored, obtained, or delivered therefrom.

"Recharging" refers to treating a sorbent material to restore a functional capacity of the sorbent material to put the sorbent material back into a condition for reuse or use in a new dialysis session. In some instances, the total mass, weight and/or amount of "rechargeable" sorbent materials remain the same. In some instances, the total mass, weight and/or amount of "rechargeable" sorbent materials change. Without being limited to any one theory of invention, the recharging process may involve exchanging ions bound to the sorbent material with different ions, which in some instances may increase or decrease the total mass of the system. However, the total amount of the sorbent material will in some instances be unchanged by the recharging process. Upon a sorbent material undergoing "recharging," the sorbent material can then be said to be "recharged."

A "recharging flow path" is a path through which fluid can travel while recharging sorbent material in a reusable sorbent module.

The term "saturated" refers to a solution having the maximum concentration of at least one solute at a given temperature.

The term "sensor," as used herein, can be a converter of any type that can measure a physical property or quantity of a matter in a solution, liquid or gas, and can convert the measurement into a signal which can be read by an electronic instrument.

The term "sodium acetate" refers to $NaCH_3CO_2H$, either in solution or solid form.

The term "sodium bisulfate" refers to $NaHSO_4$, either in solution or solid form The term "sodium chloride" refers to NaCl, either in solution or solid form.

The term "sodium citrate" refers to $Na_3C_6H_5O_7$, either in solution or solid form.

The term "sodium diacetate" refers to $NaH(C_2H_3O_2)_2$, either in solution or solid form.

The term "sodium hydroxide" refers to NaOH, either in solution or solid form.

The term "sodium phosphate" refers to $Na_2HPO_4$, either in solution or solid form.

The term "sodium salt" refers to an ionic compound containing at least one sodium ion and at least one anionic counter ion.

A "sodium source" is a solid, fluid, or concentrate source from which a solution containing sodium ions can be obtained.

The term "solid" refers to a material in the solid phase of matter, and can include crystalline, powdered, or any other form of solid material.

A "sorbent cartridge module" or "sorbent module" means a discreet component of a sorbent cartridge. Multiple sorbent cartridge modules can be fitted together to form a sorbent cartridge of two, three, or more sorbent cartridge modules. The "sorbent cartridge module" or "sorbent module" can contain any selected materials for use in sorbent dialysis and may or may not contain a "sorbent material" or adsorbent, but less than the full complement of sorbent materials needed. In other words, the "sorbent cartridge module" or "sorbent module" generally refers to the use of the "sorbent cartridge module" or "sorbent module" in sorbent-based dialysis, e.g., REDY (REcirculating DYalysis), and not that a "sorbent material" that is necessarily contained in the "sorbent cartridge module" or "sorbent module."

A "sorbent recharger" or "recharger" is an apparatus designed to recharge at least one sorbent material.

The term "source" generally refers to any component, reservoir, fluid line, section, or process by which a particular component can enter a system, section, component, or part of a system. The term is given the broadest meaning and includes any type of device or process that can introduce a component.

The term "specified concentration" refers to a concentration of one or more solutes in a solution that is predetermined per the requirements of a system or process.

The term "sulfuric acid" refers to $H_2SO_4$, either in solution or solid form.

A "water source" is a fluid source from which water can be obtained.

"Zirconium oxide" is a sorbent material that removes anions from a fluid, exchanging the removed anions for different anions. Zirconium oxide may also be referred to as hydrous zirconium oxide.

"Zirconium phosphate" is a sorbent material that removes cations from a fluid, exchanging the removed cations for different cations.

Zirconium Phosphate Recharge Solution Mixing

Figure 1B:
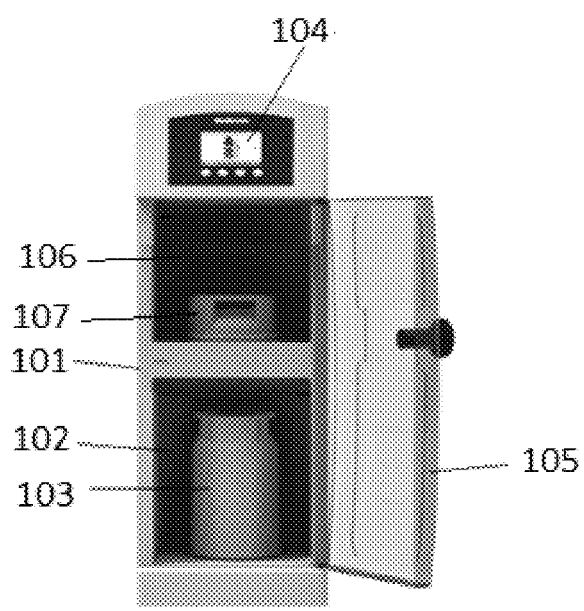
FIG. 1B shows a sorbent recharger for recharging zirconium phosphate and zirconium oxide in sorbent modules.

The invention is drawn to systems and methods for recharging and reusing zirconium phosphate in a reusable sorbent module. FIGS. 1A-B illustrate sorbent rechargers for recharging zirconium phosphate in a reusable zirconium phosphate sorbent module. FIG. 1A illustrates a sorbent recharger 101 for recharging zirconium phosphate in a zirconium phosphate sorbent module 103. FIG. 1B illustrates a sorbent recharger 101 for recharging both zirconium phosphate in a zirconium phosphate sorbent module 103 and zirconium oxide in a zirconium oxide sorbent module 107. The zirconium phosphate sorbent module 103 can be placed in a receiving compartment 102 of the sorbent recharger 101. Fluid lines (not shown) are fluidly connectable to an inlet and an outlet of the zirconium phosphate sorbent module 103. The fluid lines are also fluidly connectable to one or more recharge solution sources (not shown). The recharge solution sources contain a sodium source, an acid source, or mixtures thereof. Any source of sodium ions and an acid can be used. Non-limiting examples of the sodium salt in the sodium source can include sodium chloride, sodium acetate, sodium phosphate, sodium citrate, and sodium hydroxide. Non-limiting examples of acids that can be used include acetic acid, phosphoric acid, sulfuric acid, and citric acid. In certain embodiments, a single compound can serve as the acid source and the sodium source, such as sodium diacetate, monosodium citrate, monosodium phosphate, sodium bisulfate, or other compounds that act as both an acid and a sodium salt. The sodium and hydrogen ions in the recharge solution displace potassium, calcium, magnesium, and ammonium ions bound to the zirconium phosphate during treatment. A door 105 controls access to the receiving compartment 102 and can be opened to insert or remove the zirconium phosphate sorbent module 103 from the receiving compartment 102. The sorbent recharger 101 can also include a user interface 104 allowing a user to control the recharging of the zirconium phosphate sorbent module 103. A programmable controller (not shown) can control one or more pumps and valves (not shown) in communication with the fluid lines to control the movement of fluid through the sorbent recharger 101 and zirconium phosphate sorbent module 103.

As illustrated in FIG. 1B, the sorbent recharger 101 can include a second receiving compartment 106 for receiving a zirconium oxide sorbent module 107. Fluid lines (not shown) are fluidly connectable to an inlet and an outlet of the zirconium oxide sorbent module 107. The fluid lines are also fluidly connectable to one or more recharge solution sources (not shown) for recharging the zirconium oxide. Zirconium oxide can be recharged using recharge solutions having a hydroxyl source and a free chloride source, such as sodium hydroxide or mixtures of sodium hydroxide and sodium hypochlorite. Alternatively, potassium hydroxide or mixtures of potassium hydroxide and potassium hypochlorite can be used. The introduction of fluid from one source can occur by any differential, displacement, or motive force known to those of skill. For example, a pump can be used to introduce fluid into any one of a fluid line, compartment, or section of any part of the invention. The pumps can be positive or negative displacement pumps using pistons, diaphragms, rollers and the like. The pumps can be operated with controllers and valves to control the rate at which fluid can be introduced, conveyed, or moved from one location to another. The pumps can be pulsatile or non-pulsatile. One of ordinary skill will appreciate that many components, means, devices, and methods are available for introducing fluid from one section to another.

One or more of the recharge solutions can be used for recharging both the zirconium phosphate and the zirconium oxide. For example, a water source and a sodium hydroxide source can be included in both a zirconium phosphate recharging flow path and a zirconium oxide recharging flow path. A single recharge solution source can be fluidly connected to each recharging flow path or separate recharge solution sources can be used for each recharging flow path. One of skill in the art will understand that sorbent rechargers can be constructed with any number of receiving compartments for recharging any number of sorbent modules. A sorbent recharger can include multiple receiving compartments each for recharging zirconium phosphate sorbent modules, or multiple receiving compartments for recharging any combination of zirconium phosphate and zirconium oxide sorbent modules.

Figure 2:
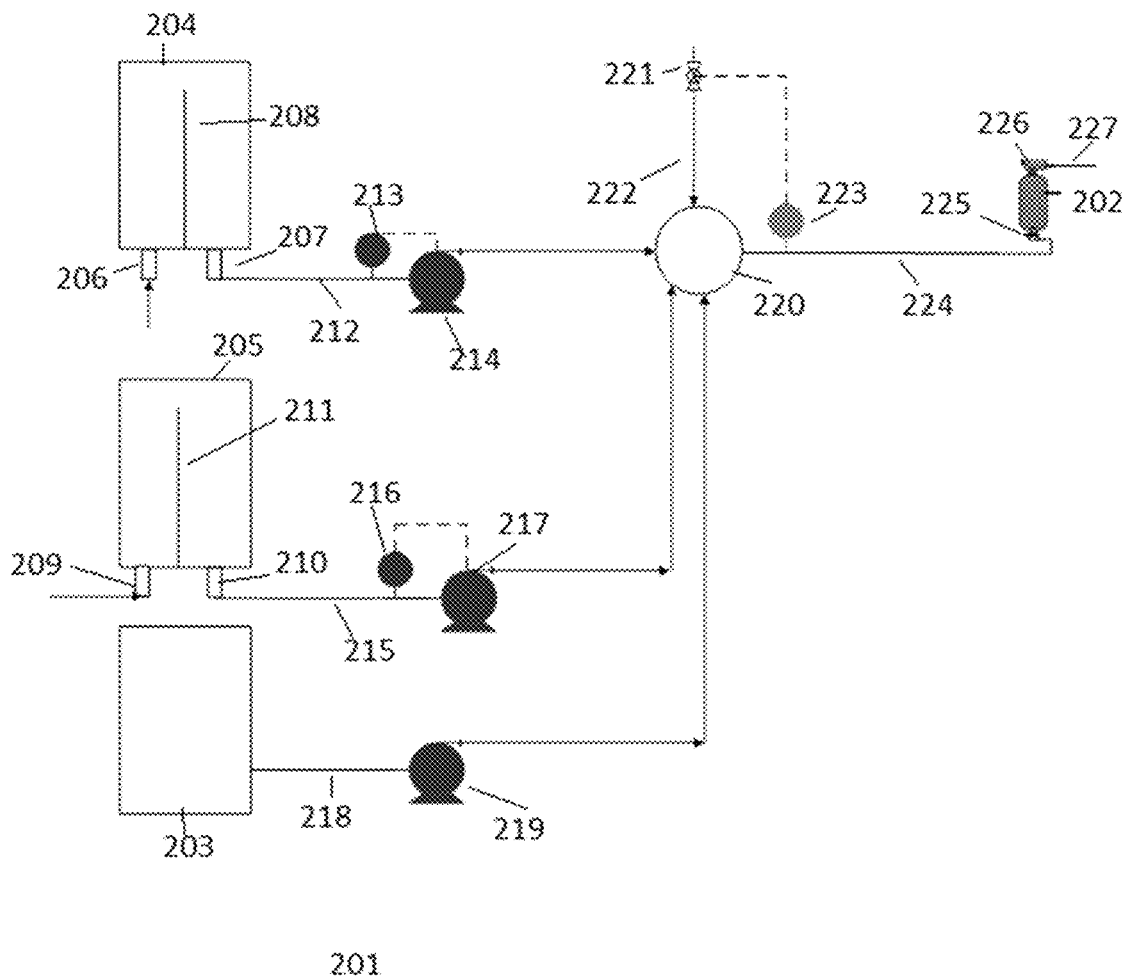
FIG. 2 shows a recharging flow path for recharging zirconium phosphate with a sodium source, a base source, and an acid source in partitioned bags.

FIG. 2 illustrates a non-limiting embodiment of a recharging flow path 201 for generating a recharge solution and introducing the recharge solution through a zirconium phosphate sorbent module 202. The recharging flow path 201 can include a sodium source 204, and an acid source 203. In certain embodiments, a base source 205 can also be included for control over the pH of the recharge solutions. As described, the sodium source 204 can contain a sodium salt, such as sodium chloride, the acid source 203 can contain an acid, such as acetic acid, and the base source 205 can contain a sodium salt of the conjugate base in the acid in the acid source 203, such as sodium acetate. In certain embodiments, the base source 205 can be eliminated. In certain embodiments, the sodium source 204 can be eliminated, and the base source 205 can serve as the sodium source. Mixing a sodium base, such as sodium hydroxide, with the acid in a specified ratio can create a buffer solution having specified concentrations of sodium and acid needed for recharging the zirconium phosphate and obtaining a desired zirconium phosphate pH. A source of a compound that can serve as both a sodium salt and an acid, such as a sodium diacetate source, can be used in addition, or as an alternative, to the base source 205 and the acid source 203. As illustrated in FIG. 2, any one or more of the recharge solution sources can be provided in a partitioned bag. A partitioned bag is a recharge solution source that initially contains a solid material. Water is added to the partitioned bag to dissolve the solid material, generating the recharge solution. The partitioned bag can be flexible, semi-rigid, or rigid. The partitioned bag can be constructed from any appropriate material suitable for retaining a solid and aqueous form of any one of a sodium salt solution, a base solution, an acid solution, and similar chemicals.

Water from a water source (not shown) can be introduced to the sodium source 204 through water inlet 206. The water dissolves solid sodium salt in the sodium source 204, and the resulting sodium solution can exit partitioned bag through solution outlet 207 into fluid line 212. A separator 208 can be included in sodium source 204 to prevent solid salts from reaching the solution outlet 207. Similarly, water can be introduced into base source 205 by water inlet 209. The water can dissolve the base within the base source 205 and exit through solution outlet 210 into fluid line 215. Separator 211 prevents solid base from reaching solution outlet 210 and fluid line 215. Although the acid source 203 is shown as a single bag containing liquid acid, one of skill in the art will understand that a partitioned bag can also be used for the acid. However, if acetic acid is used as the acid source, a partitioned bag is unnecessary because acetic acid is a liquid at room temperature. When a liquid acid is used, the acid source 203 can be a flexible bag similar to the partitioned bag without a water inlet, a plastic bottle, or any other acid source. Alternatively, a pre-mixed acid solution can be used in place of the acid source 203. Optionally, a mesh or screen can be placed over the solution outlet 207 or solution outlet 210 to prevent solid material from exiting. The optional screen mesh can be used with or without separator 208 or separator 211.

The sodium source 204 and base source 205 can be used to generate saturated solutions of sodium salts. To generate a saturated solution of a sodium salt, the system only requires to be maintained at a minimum level of solid sodium salt in sodium source 204. As water is introduced through water inlet 206, the water will dissolve sodium salt, forming a saturated sodium chloride solution. A saturated base solution can be generated in the same manner using base source 205. Advantageously, using saturated solutions allows for the concentration of sodium or base to be estimated or approximately known based on an assumed temperature.

To generate the recharge solution for recharging the zirconium phosphate in zirconium phosphate sorbent module 202, a sodium solution from sodium source 204 is introduced to mixer 220 via fluid line 212. Mixer 220 can be either a dynamic or static mixer. A dynamic mixer can include one or more components that agitate or stir solutions, while a static mixer can use passive mixing that relies on a shape or inherent feature of the fluid compartment or section in which the fluid is being mixed. For example, shaped contours or bends in the fluid compartment or section can provide passive mixing. Pump 214 can provide the driving force necessary to move the sodium chloride solution through fluid line 212. A sensor 213 can be included to measure the sodium concentration in fluid line 212 and ensure that a saturated solution is being introduced into the mixer 220. A controller (not shown) can receive data from the sensor 213 and adjust the flow rate of sodium solution through fluid line 212 if necessary by changing the pump rate of pump 214. Base solution is introduced to the mixer 220 through fluid line 215. Pump 217 can provide the driving force necessary to move the base solution through fluid line 215. A sensor 216 can be included to measure the base concentration in fluid line 215 and ensure that a saturated solution is being introduced into the mixer 220. The controller can receive data from the sensor 216 and adjust the flow rate of the base solution through fluid line 215 if necessary by changing the pump rate of pump 217. Acid is introduced to mixer 220 by fluid line 218. In certain embodiments, the base solution can be eliminated, and only an acid and sodium solution used. In certain embodiments, the sodium solution can be eliminated, and only an acid and base solution used where the recharge solution is generated by mixing the base with the acid.

In mixer 220, the sodium solution, base solution, and acid solutions are mixed. Water from a water source (not shown) can be introduced to mixer 220 to dilute the recharge solution. The recharge solution introduced into zirconium phosphate sorbent module 202 can have a desired concentration of sodium and acid. The relative amounts of sodium ions to hydrogen ions in the recharge solution can determine the relative amounts of sodium and hydrogen adsorbed by the zirconium phosphate and released during a subsequent dialysis session. A controller (not shown) can control the flow rates of acid, sodium solution, base, and water introduced to mixer 220 to maintain the concentrations of sodium and acid or the pH of the recharge solution within a predetermined range. The flow rate of sodium solution is controlled by pump 214, the flow rate of the base solution is controlled by pump 217, the flow rate of the acid solution is controlled by pump 219, and the flow rate of water can be controlled by using valve 221. Alternatively, a pump rate of a pump used to introduce water into the mixer 220 can be controlled to dilute the recharge solution to the desired concentration. The sensors illustrated in FIG. 2 can be conductivity sensors, pH sensors, or combinations thereof.

The recharge solution can exit the mixer 220 through fluid line 224 and can be introduced to zirconium phosphate sorbent module 202 through zirconium phosphate module inlet 225. A sensor 223 can be used to measure the concentration of sodium and acid in fluid line 224. If the concentration of sodium and acid or if the pH is not within a predetermined range, the controller can adjust the flow rates of the sodium solution, the base solution, the acid solution, and/or water as necessary to maintain the sodium concentration, acid concentration and pH, in the recharging fluid within a predetermined range of a specified concentration. The recharge solution exits zirconium phosphate sorbent module 202 by zirconium phosphate module outlet 226 into effluent line 227, which can be fluidly connected to a drain or waste reservoir.

In certain embodiments, the sodium and acid used to generate the recharge solution can also be used to disinfect the zirconium phosphate sorbent module 202. However, disinfecting with sodium and acid solutions can require elevated temperatures and disinfection times. As an alternative, a peracetic acid solution can be used to disinfect the zirconium phosphate sorbent module 202. In certain embodiments, a peracetic acid solution can be generated from an acid source and a peroxide source, such as acetic acid and hydrogen peroxide. For example, the acid source 203 can contain acetic acid and an additional hydrogen peroxide source (not shown) can be included. The acetic acid and hydrogen peroxide can be mixed to generate a disinfection solution containing peracetic acid, which can reduce the necessary temperature or time for disinfection of the zirconium phosphate sorbent module 202. In addition, a separate prepared source of peracetic acid solution can be used.

As an alternative to the system illustrated in FIG. 2, any one or more of the recharge solution sources can be provided as a pre-mixed concentrate rather than as a solid. The pre-mixed concentrate can be fluidly connected to a sorbent recharger in place of the partitioned bag illustrated in FIG. 2. Alternatively, plastic bottles or other reservoirs can be used in place of bags. Further, any one or more of the recharge solution sources can be combined. For example, a pre-mixed liquid buffer concentrate of an acid and the sodium salt of the conjugate base, such as sodium acetate and acetic acid, can be used in place of separate acid and base sources. Water can be introduced into the sodium source 204 to produce a saturated sodium chloride solution, and the saturated sodium solution can be dosed by adding the pre-mixed liquid buffer to generate a saturated sodium/buffer solution, and then diluted as illustrated. Alternatively, a pre-mixed concentrate of sodium and base or sodium and a combined acid/sodium source, such as sodium diacetate or a mixture of sodium acetate and sodium diacetate, can be used, which is then dosed with acid to generate the recharge solution. In certain embodiments, mixer 220 can be eliminated, with the sodium solution, base solution, and acid mixing in fluid line 224 as the solutions are added.

Figure 3:
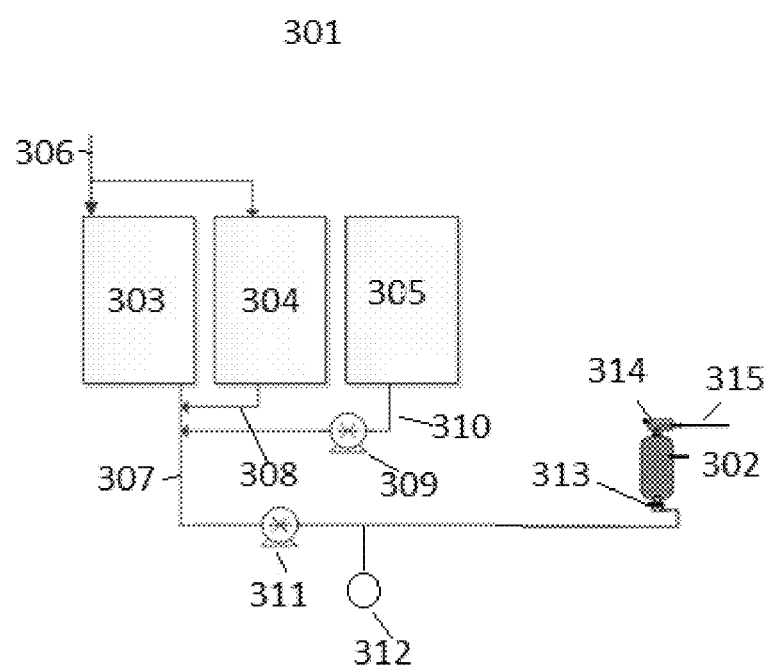
FIG. 3 shows a recharging flow path for recharging zirconium phosphate with sodium, base, and acid tanks.

FIG. 3 illustrates a non-limiting embodiment of a recharging flow path 301 for generating a recharge solution and introducing the recharge solution through a zirconium phosphate sorbent module 302. The recharge solution sources can include a sodium source 303, a base source 304, and an acid source 305. In certain embodiments, the base source 304 and acid source 305 can be replaced by a combined sodium/acid source, such as a sodium diacetate source, a recharge solution source containing a mixture of sodium acetate and sodium diacetate or a mixture of sodium diacetate and acetic acid. Using sodium acetate or both sodium acetate and sodium diacetate can provide greater flexibility and allow for a buffer composition of acetate/acetic acid greater than 1. Using sodium diacetate and acetic acid can also provide flexibility and allow a buffer composition of acetate/acetic acid less than one. The sodium source 303 and base source 304 can be rigid tanks initially containing solid sodium salt and solid base. Water from a water source (not shown) can be introduced to sodium source 303 and base source 304 through water inlets from fluid line 306. The resulting sodium solution can exit the sodium source 303 through fluid line 307. Base solution can exit base source 304 through fluid line 308 and mix with the sodium solution generating a basic sodium solution. In certain embodiments, the generated basic sodium solutions can be saturated solutions. To generate saturated solutions, a user need only maintain a minimum amount of solid base and solid sodium salt in the tanks. The water will dissolve the salts, and so long as solid salt remains, the resulting solution will be saturated. Additional water from a water source can be added when using a saturated sodium acetate and saturated sodium chloride solution to prevent precipitation of sodium. Because the mixture of sodium chloride and sodium acetate has a lower solubility than the individual solutions, additional water for dilution is needed to prevent precipitation. To control the pH of the recharge solution, acid from acid source 305 can be introduced to fluid line 307 via fluid line 310. In certain embodiments, the acid source 305 can contain liquid acetic acid. Alternatively, the acid source 305 can contain a concentrated acid solution or a solid acid source that is dissolved with water from the water source. Pump 309 controls the flow rate of acid and can be varied to generate a recharge solution having a desired concentration of sodium and acid. Water from a water source (not shown) can be added via fluid line 316 to dilute the recharge solution as necessary. In certain embodiments, a single water source can be fluidly connected to fluid lines 316 and 306. Alternatively, separate water sources can be used. Additional pumps (not shown) can be included to control the flow rates of the water, sodium, and base solutions. A sensor 312 can measure the sodium and acid concentrations. A controller (not shown) in communication with the sensor 312 can adjust the flow rates of the sodium solution, base solution, and acid to maintain the concentration of sodium and acid within a predetermined range of a specified concentration. A dynamic or static mixer (not shown) can optionally be included to ensure complete mixing of the sodium solution, base solution, and acid. The resulting recharge solution can be introduced to the zirconium phosphate sorbent module 302 from fluid line 307 through zirconium phosphate module inlet 313. Pump 311 can provide the driving force necessary for moving the recharge solution through the recharging flow path 301. The recharge solution can exit the zirconium phosphate sorbent module 302 through zirconium phosphate module inlet 314 into effluent line 315, which can be fluidly connected to a drain or waste reservoir. An optional heater could be included to heat the recharge solution before entering zirconium phosphate sorbent module 302 because recharging of zirconium phosphate may be more efficient at elevated temperatures.

The tanks serving as sodium source 303, base source 304, and acid source 305 can be any size. In certain embodiments, the tanks can be large enough to provide recharge solutions for a single recharging of zirconium phosphate. Alternatively, larger tanks can be used, allowing multiple zirconium phosphate sorbent modules to be recharged without replacing the chemicals, or allowing a single tank to service multiple sorbent rechargers. Recirculating pumps, agitators, and/or overhead stirrers (not shown) can be used with the tanks to ensure complete mixing and generation of saturated solutions.

In certain embodiments, the partitioned bag illustrated in FIG. 2 can be used with the tanks illustrated in FIG. 3. The contents of the partitioned bag can be emptied into the tanks, allowing the user to decide whether to use tanks or bags without needing to change the source of the solutes. Additionally, the system can combine the embodiments shown in FIGS. 2-3. For example, a base source can be a partitioned bag, while the sodium source is a rigid tank.

As described, any of the recharge solution sources can be combined. For example, the sodium source 303 and base source 304 can be combined into a single brine tank to provide a single basic sodium solution. Alternatively, a single solution containing a compound serving as both a source of sodium and acid, such as a sodium acetate/sodium diacetate/sodium chloride source can be used. In certain embodiments, a pre-mixed liquid buffer can be used as a single recharge solution source. Dosing the saturated sodium solution from sodium source 303 with the pre-mixed liquid buffer can provide a saturated sodium/base, which can be diluted as necessary. In certain embodiments, a single sodium, base, and acid source can be used. The pre-mixed liquid buffer can be added directly to the sodium source 303, generating a brine solution for recharging the zirconium phosphate.

As described, an additional peroxide source, such as hydrogen peroxide, can be included for generating a disinfection solution when mixed with acetic acid in the acid source 305.

Figure 4:
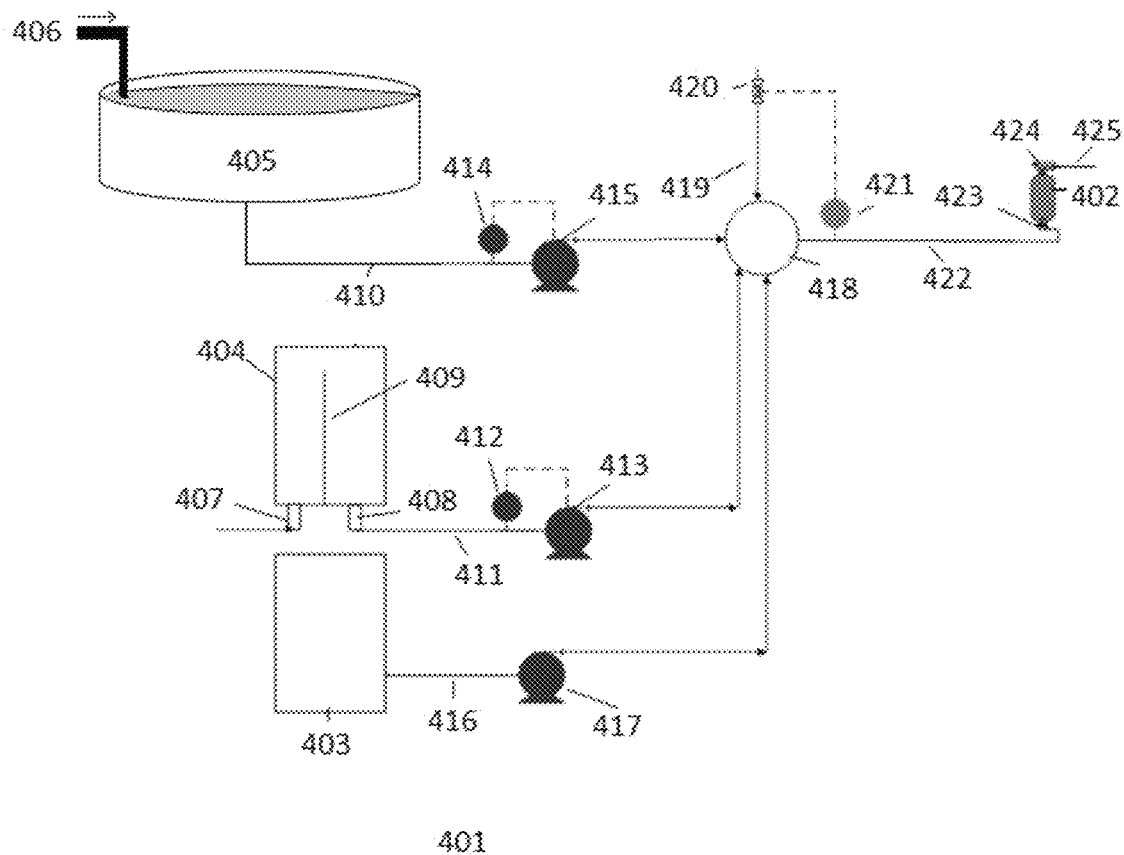
FIG. 4 shows a recharging flow path for recharging zirconium phosphate with a sodium source, an acid source, and sodium hydroxide.

FIG. 4 illustrates an alternative embodiment of a recharging flow path 401 for recharging zirconium phosphate in a zirconium phosphate sorbent module 402. The recharging flow path 401 can include a sodium source 404, and acid source 403, and a sodium hydroxide source 405. In FIG. 4, the acid source 403 is illustrated as a bag or plastic bottle, the sodium source 404 can be a partitioned bag, and the sodium hydroxide source 405 can be a tank. However, any of the recharge solution sources can be partitioned bag, flexible bags, plastic bottles, or tanks.

Water from a water source (not shown) can be introduced to the sodium source 404 through water inlet 407. The water can dissolve a solid sodium salt, such as sodium chloride, in the sodium source 404, and the resulting sodium solution can exit sodium source 404 through solution outlet 408 into fluid line 411. A separator 409 can be included in sodium source 404 to prevent solid sodium salt from reaching the solution outlet 408. Acid from acid source 403 can be introduced into fluid line 416 by pump 417. Sodium hydroxide can be introduced into fluid line 410 by pump 415. However, the sodium hydroxide source 405 can be replaced by a partitioned bag containing solid sodium hydroxide, a bag or plastic bottle containing a pre-mixed sodium hydroxide solution, or an electrolysis system that generates a sodium hydroxide solution by electrolysis of a sodium chloride solution. Advantageously, using an electrolysis system to generate sodium hydroxide can eliminate impurities, such as carbonates, from the sodium hydroxide solution and prevents the direct handling of sodium hydroxide solutions or solids. Certain acids, such as acetic acid can also be generated with an electrolysis system that converts sodium acetate into acetic acid. Advantageously, using an electrolysis system to generate acetic acid allows the use of solid sodium acetate and prevents the direct handling of concentrated acetic acid.

To generate the recharge solution for recharging the zirconium phosphate in zirconium phosphate sorbent module 402, a sodium solution from sodium source 404 is introduced to mixer 418 via fluid line 411. The mixer 418 can be either a dynamic or static mixer. Pump 413 can provide the driving force necessary to move the sodium solution through fluid line 411. A sensor 412 can be included to measure the sodium concentration in fluid line 411 and ensure that a saturated solution, or a solution of known concentration, is being introduced into the mixer 418. A controller (not shown) can receive data from the sensor 412 and adjust the flow rate of sodium solution through fluid line 411 if necessary by changing the pump rate of pump 413. Sodium hydroxide solution is introduced to the mixer 418 through fluid line 410. Pump 415 can provide the driving force necessary to move the sodium hydroxide solution through fluid line 410. A sensor 414 can be included to measure the sodium hydroxide concentration in fluid line 410 and ensure that a saturated solution, or a solution of known concentration, is being introduced into the mixer 418. The controller can receive data from the sensor 414 and adjust the flow rate of sodium hydroxide through fluid line 410 if necessary by changing the pump rate of pump 415. Acid is introduced to mixer 418 by fluid line 416. Pump 417 provides the driving force for moving acid through fluid line 416. If necessary, the controller can adjust the pump rate of pump 417 to change the flow rate of acid through fluid line 416. Sodium hydroxide solution is not introduced directly to the zirconium phosphate sorbent module 402, but is used to generate a recharge solution having specified concentrations of sodium and acid when mixed with the sodium solution and acid solution.

In certain embodiments, the sodium hydroxide in sodium hydroxide source 405 can be a saturated sodium hydroxide solution. Advantageously, using a saturated sodium hydroxide solution allows for the sodium hydroxide to have a known concentration without the need for additional sensors. To generate and maintain a saturated sodium hydroxide solution in sodium hydroxide source 405, the user need only maintain a minimum amount of solid sodium hydroxide within the sodium hydroxide source 405. Water can be added to the sodium hydroxide source 405 by water inlet 406 as needed. If the amount of solid sodium hydroxide in sodium hydroxide source 405 is too low, additional solid sodium hydroxide can be added. A saturated solution of sodium hydroxide can be maintained by adding less than an amount of water necessary to dissolve the solid sodium hydroxide to sodium hydroxide source 405. Further, the heat of dissolution of the sodium hydroxide can increase the temperature of the recharge solution, aiding in the recharging process. Because recharging zirconium phosphate may be more efficient at elevated temperatures, a heater can be added to any embodiment. The heat of dissolution of the sodium hydroxide, by raising the temperature of the recharge solution, can reduce the burden on the heater.

In mixer 418, the sodium solution, sodium hydroxide, and acid solutions are mixed. Water from a water source (not shown) can be introduced to mixer 418 to dilute the recharge solution via fluid line 419. The controller can control the flow rates of acid, sodium solution, sodium hydroxide, and water introduced to mixer 418 to maintain the concentrations of sodium and acid within a predetermined range of a specified concentration. The flow rate of sodium solution can be controlled by pump 413, the flow rate of sodium hydroxide can be controlled by pump 415, the flow rate of the acid can be controlled by pump 417, and the flow rate of water can be controlled by using valve 420. Alternatively, a pump rate of a pump used to introduce water into the mixer 418 can be controlled to dilute the recharge solution to the desired concentration. The sensors illustrated in FIG. 4 can be conductivity sensors, pH sensors, or combinations thereof.

The recharge solution can exit the mixer 418 through fluid line 422 and can be introduced to zirconium phosphate sorbent module 402 through zirconium phosphate module inlet 423. A sensor 421 can be used to measure the concentration of sodium and acid in fluid line 422. If the concentration of sodium, acid, and/or pH is not within a predetermined range, the controller can adjust the flow rates of sodium solution, acid, sodium hydroxide, and/or water as necessary. The recharge solution exits zirconium phosphate sorbent module 402 by zirconium phosphate module outlet 424 into effluent line 425, which can be fluidly connected to a drain or waste reservoir. In certain embodiments, mixer 418 can be eliminated, with the sodium hydroxide, sodium solution, and acid mixing in fluid line 422 as the solutions are introduced.

As described, an additional peroxide source (not shown), such as hydrogen peroxide, can be included for generating a disinfection solution when mixed with acetic acid in the acid source 403.

One skilled in the art will understand that various combinations and/or modifications and variations can be made in the described systems and methods depending upon the specific needs for operation. Moreover, features illustrated or described as being part of an aspect of the invention may be used in the aspect of the invention, either alone or in combination, or follow a preferred arrangement of one or more of the described elements.

We claim:

1. A system, comprising:
a sorbent recharger having a recharging flow path comprising at least one receiving compartment for a zirconium phosphate sorbent module; the at least one receiving compartment comprising a zirconium phosphate module inlet and a zirconium phosphate module outlet;
at least one recharge solution source; the at least one recharge solution source comprising an acid source and a sodium source; and
a controller controlling at least one pump to introduce fluid from the at least one recharge solution source through the zirconium phosphate sorbent module.

2. The system of claim 1, the at least one recharge solution source further comprising a base source.

3. The system of claim 1, wherein the sodium source is selected from the group consisting of sodium chloride, sodium acetate, sodium phosphate, sodium citrate, sodium hydroxide, and combinations thereof, and the acid source is selected from the group consisting of acetic acid, phosphoric acid, sulfuric acid, citric acid, and combinations thereof.

4. The system of claim 1, wherein the sodium source and acid source is selected from sodium diacetate, monosodium citrate, monosodium phosphate, sodium bisulfate, and combinations thereof.

5. The system of claim 1, wherein the at least one recharge solution source comprises a source of solid sodium salt, solid acid, and/or solid sodium salt and solid acid.

6. The system of claim 3, wherein the source of solid sodium salt, solid acid, and/or solid sodium salt and acid comprises a partitioned bag containing solid sodium salt, solid acid, and/or solid sodium salt and solid acid.

7. The system of claim 6, wherein the partitioned bag containing solid sodium salt, solid acid, and/or solid sodium salt and solid acid comprises an inlet fluidly connectable to a water source and an outlet fluidly connectable to the recharging flow path.

8. The system of claim 1, wherein the at least one recharge solution source comprises a saturated source of a sodium salt.

9. The system of claim 3, wherein at least one recharge solution source comprises a saturated source of sodium acetate.

10. The system of claim 3, wherein at least one recharge solution source comprises a liquid acid.

11. The system of claim 1, further comprising a water source fluidly connected to the recharging flow path.

12. The system of claim 3, wherein at least one recharge solution source comprises sodium hydroxide.

13. The system of claim 1, further comprising a mixer fluidly connected to the recharging flow path.

14. The system of claim 1, further comprising at least one sensor fluidly connected the recharging flow path.

15. The system of claim 1, further comprising a second recharging flow path comprising a second receiving compartment for a zirconium oxide sorbent module; the second receiving compartment comprising a zirconium oxide module inlet and a zirconium oxide module outlet; and at least a second recharge solution source; the at least second recharge solution source containing at least a hydroxyl source and a free chlorine source.

16. The system of claim 14, wherein the at least one sensor is a conductivity sensor.

17. The system of claim 14, wherein the at least one sensor is a pH sensor.

* * * * *